United States Patent
Polidoro et al.

[11] Patent Number: 6,146,337
[45] Date of Patent: Nov. 14, 2000

[54] HOLDER FOR BLOOD COLLECTION NEEDLE WITH BLUNTING MECHANISM

[75] Inventors: John M. Polidoro, Coventry; Walter Hauri, Putnam; P. Spencer Kinsey, Newington; Richard G. Holdaway, Storrs; Carl R. Sahi, Coventry, all of Conn.

[73] Assignee: Bio-Plexus, Inc., Vernon, Conn.

[21] Appl. No.: 09/199,742

[22] Filed: Nov. 25, 1998

[51] Int. Cl.[7] .............................. A61B 5/00; B65D 81/00
[52] U.S. Cl. ............................................................ 600/576
[58] Field of Search .............................. 600/576; 604/170

[56] References Cited

U.S. PATENT DOCUMENTS

| | | |
|---|---|---|
| 1,527,291 | 2/1925 | Zorraquin . |
| 2,623,520 | 12/1952 | Bamford, Jr. et al. .................. 128/221 |
| 2,623,521 | 12/1952 | Shaw ...................................... 128/221 |
| 3,840,008 | 10/1974 | Noiles ..................................... 128/221 |
| 3,923,066 | 12/1975 | Francisoud et al. ..................... 128/348 |
| 4,535,773 | 8/1985 | Yoon .......................................... 604/51 |
| 4,613,329 | 9/1986 | Bodicky .................................. 604/158 |
| 4,664,654 | 5/1987 | Strauss .................................... 604/198 |
| 4,675,005 | 6/1987 | DeLuccia ................................ 604/110 |
| 4,747,831 | 5/1988 | Kulli ....................................... 604/110 |
| 4,778,453 | 10/1988 | Lopez ..................................... 604/110 |
| 4,790,828 | 12/1988 | Dombrowski et al. ................. 604/198 |
| 4,795,432 | 1/1989 | Karczmer ............................... 604/110 |
| 4,804,371 | 2/1989 | Vaillancourt ........................... 604/198 |
| 4,808,168 | 2/1989 | Warring .................................. 604/158 |
| 4,813,426 | 3/1989 | Haber et al. ............................ 128/763 |
| 4,869,717 | 9/1989 | Adair ........................................ 604/51 |
| 4,978,344 | 12/1990 | Dombrowski et al. ................. 604/198 |
| 5,009,642 | 4/1991 | Sahi ........................................ 604/158 |
| 5,030,208 | 7/1991 | Novacek et al. ....................... 604/195 |
| 5,098,402 | 3/1992 | Davis ...................................... 604/195 |
| 5,104,381 | 4/1992 | Gresl et al. ............................. 604/164 |
| 5,104,382 | 4/1992 | Brinkerhoff et al. ................... 604/165 |
| 5,139,485 | 8/1992 | Smith et al. ............................ 604/158 |
| 5,190,050 | 3/1993 | Nitsche .................................. 128/772 |
| 5,201,710 | 4/1993 | Caselli .................................... 604/110 |
| 5,226,426 | 7/1993 | Yoon ....................................... 128/753 |
| 5,256,148 | 10/1993 | Smith et al. ............................ 604/158 |
| 5,330,432 | 7/1994 | Yoon ....................................... 604/164 |
| 5,334,159 | 8/1994 | Turkel .................................... 604/158 |
| 5,336,176 | 8/1994 | Yoon ......................................... 604/51 |
| 5,364,365 | 11/1994 | Wortrich ................................. 604/158 |
| 5,374,252 | 12/1994 | Banks et al. ........................... 604/158 |
| 5,423,760 | 6/1995 | Yoon ....................................... 604/165 |
| 5,423,770 | 6/1995 | Yoon ....................................... 604/281 |
| 5,476,106 | 12/1995 | Gartz ...................................... 128/898 |
| 5,478,317 | 12/1995 | Yoon ....................................... 604/165 |

(List continued on next page.)

FOREIGN PATENT DOCUMENTS

| | | | |
|---|---|---|---|
| 0 405 883 A2 | 1/1991 | European Pat. Off. | ........ A61B 17/34 |
| 2 147 183 | 4/1973 | Germany | ......... A61M 5/18 |
| 802351 | 10/1958 | United Kingdom . | |

*Primary Examiner*—Max Hindenburg
*Assistant Examiner*—Brian Szmal
*Attorney, Agent, or Firm*—Libert & Associates; Frederick A. Spaeth

[57] ABSTRACT

The present invention relates to a self-blunting blood collection needle (55) in which a blunting member (26*a*) is deployed upon withdrawal of a blood collection tube (56*a*) from the tube holder (e.g., 136), to blunt the needle (22) and so safeguard the patient and the technician from inadvertent needle sticks. The blunting member (26*a*) is retracted to re-sharpen the needle (22) when a subsequent collection tube is inserted into the holder (136). The deployment and retraction of the blunting member (26*a*) is accomplished with a mechanism (142) that is responsive to the insertion and withdrawal of the blood collection tube (56*a*) to retract and deploy the blunting member (26*a*) accordingly. One feature of the present invention is that the mechanism (142) effects blunting and re-sharpening of the needle without requiring that the technician manipulate the mechanism in a manner different from that of conventional, non-blunting collection needles. Four mechanisms are disclosed: a rack and pinion mechanism (42); a cylindrical cam mechanism (142); a lever mechanism (242) and a reversing strap mechanism (342).

23 Claims, 15 Drawing Sheets

U.S. PATENT DOCUMENTS

| | | | |
|---|---|---|---|
| 5,549,564 | 8/1996 | Yoon | 604/165 |
| 5,562,629 | 10/1996 | Haughton et al. | 604/158 |
| 5,586,991 | 12/1996 | Yoon | 606/185 |
| 5,634,934 | 6/1997 | Yoon | 606/185 |
| 5,645,556 | 7/1997 | Yoon | 606/185 |
| 5,665,072 | 9/1997 | Yoon | 604/164 |
| 5,718,239 | 2/1998 | Newby et al. | 128/763 |
| 5,779,680 | 7/1998 | Yoon | 604/164 |

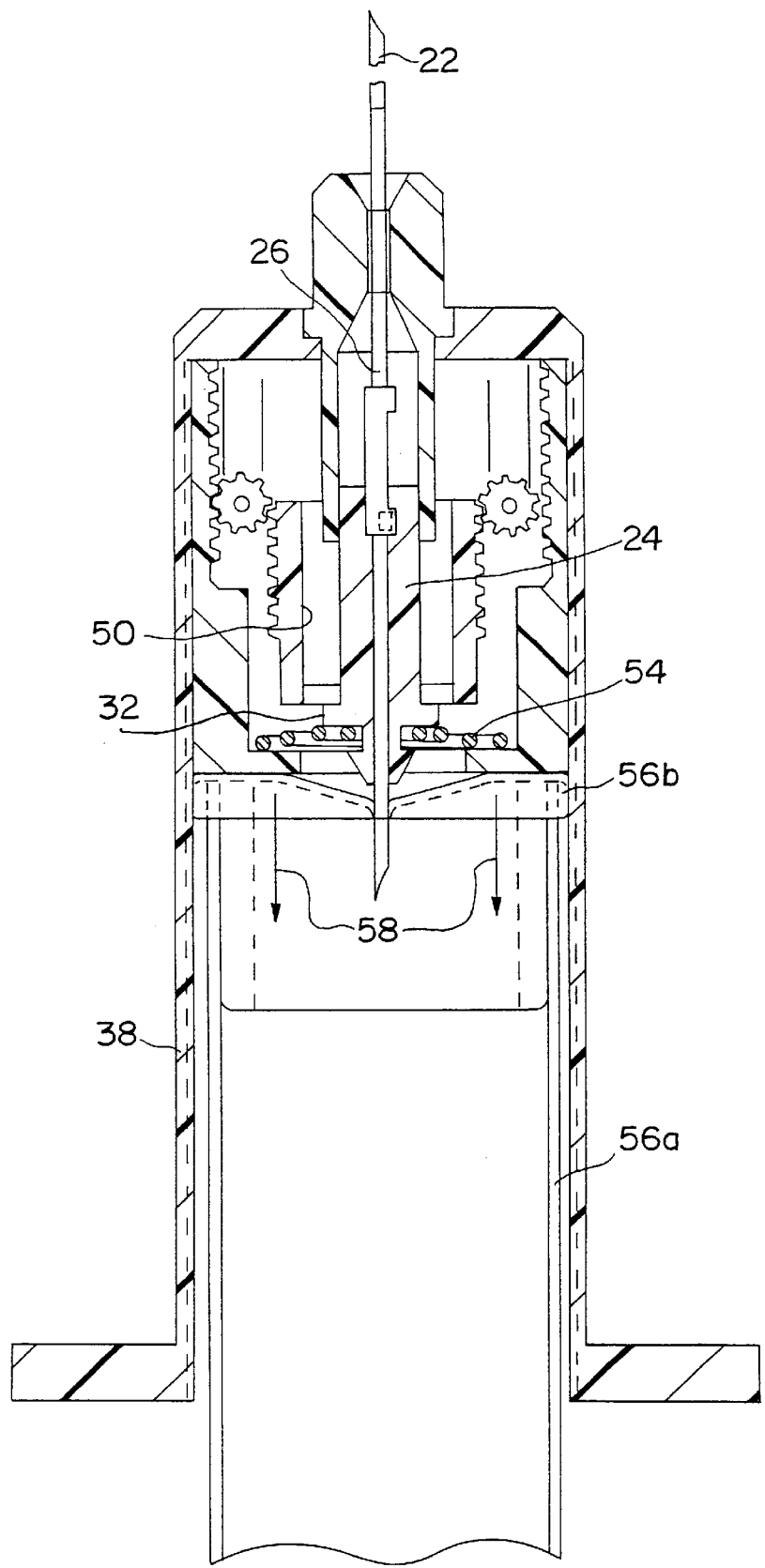
F I G. 4A

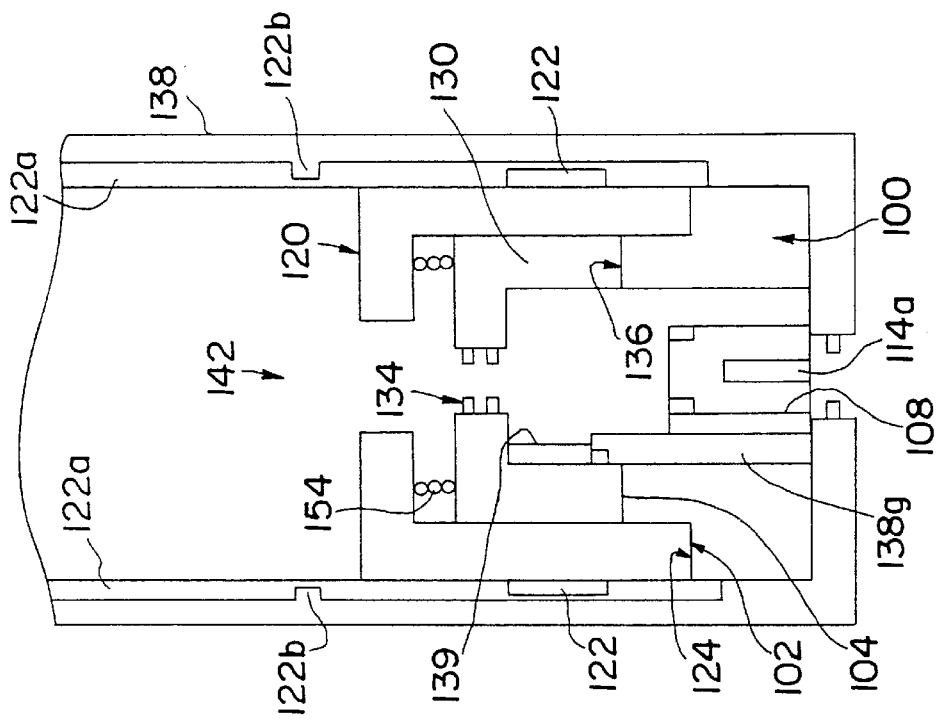
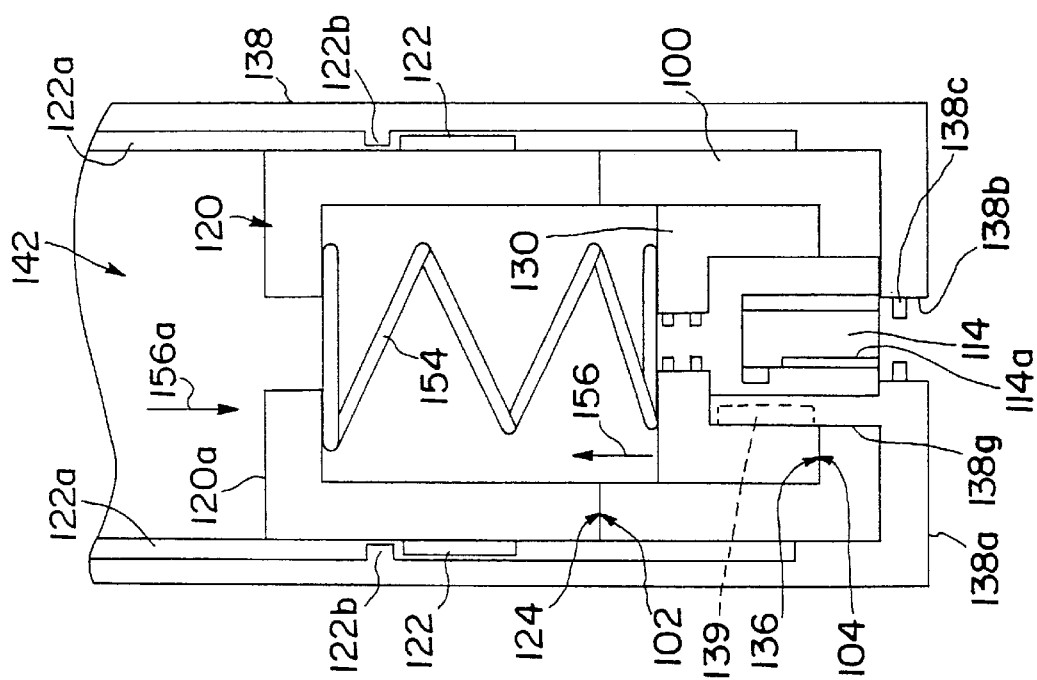

ary link member may comprise a lever pivotably mounted in the holder for rotation about a fulcrum point. The lever may have arms extending from the fulcrum point, one arm being attached to the transmitter member and another arm being connected to the actuator member.

HOLDER FOR BLOOD COLLECTION NEEDLE WITH BLUNTING MECHANISM

BACKGROUND OF THE INVENTION

Field of the Invention

The present invention pertains to self-blunting needle devices and, in particular, to holders for blood collection needles.

Conventional blood collection systems are known in the art to comprise a holder, typically in the form of a generally cylindrical shell, that holds a double-ended needle cannula. One end of the needle cannula extends forward from the holder and is used for venipuncture (the "venipuncture needle") while the other end (the "filling needle") extends into the holder and is used to puncture the seal cap on a sample fluid collection tube (which, typically, is vacuum-sealed). The device is used by unsheathing the venipuncture needle and effecting venipuncture and then inserting the sealed end of a collection tube into the holder and pushing the seal cap against the boot that covers the tip of the filling needle. The filling needle pierces the boot and the seal cap and blood is drawn into the collection tube. If additional samples are required, the first collection tube is removed and a second collection tube is pushed into the holder in its place. When the last tube is filled, the blood collection needle is withdrawn from the patient's vein.

Prior art self-blunting blood collection needles have provided a deployable, locking, blunting member to protect the user against inadvertent needle sticks but required the user to engage in an extraneous manipulation of the sample tube in order to deploy the blunting member such as the insertion of the sample tube past a discernible "stop" point at which the collection tube is already fully engaged by the filling needle. There is need, therefore, for a self-blunting needle mechanism that does not require manipulation beyond that which is familiar to medical technicians with the use of conventional blood collection needles.

SUMMARY OF THE INVENTION

The present invention provides a needle holder apparatus comprising a holder for a needle assembly having a needle cannula and a movable blunting member. The holder is dimensioned and configured for receiving and holding a sample collection tube in fluid flow communication with such needle assembly. There is also a mechanism in the holder comprising a movable actuator member configured and situated for engaging a blunting member, a movable transmitter member and means for moving the actuator in the holder in opposite directions from that of the transmitter member.

According to one aspect of this invention, the apparatus may further comprise a biasing member positioned to be tensioned against the transmitter member when the transmitter member and the actuator member move to bias the mechanism to reverse such motion.

According to another aspect of the invention, the holder may comprise a shell having a cylindrical interior and the reversing link member may comprise a cylindrical cam member rotatably disposed in the holder. The reversing link member may comprise a pair of counter-spiraled cam regions, and the transmitter member may engage one cam region and the actuator member engages the other cam region.

According to a further aspect of the invention, the reversing link member may comprise a pinion and the transmitter member and the actuator member may each comprise a rack for engaging the pinion.

According to yet another aspect of the invention, the reversing link member may comprise a lever pivotably mounted in the holder for rotation about a fulcrum point. The lever may have arms extending from the fulcrum point, one arm being attached to the transmitter member and another arm being connected to the actuator member.

According to still another aspect of the invention, the reversing link member may comprise a pliable, resilient strap.

The present invention also provides a blood collection needle comprising a needle assembly comprising a needle cannula and a blunting member. The needle cannula has a puncture tip and a needle passageway therethrough and the blunting member has a blunt end. The needle cannula and the blunting member are disposed telescopically one within the other without obstructing flow through the needle passageway. The needle assembly is movable between an insertion configuration in which the puncture tip of the needle cannula is exposed and a blunted configuration in which the blunt end of the blunting member extends beyond the puncture tip to blunt the apparatus.

The needle assembly is mounted in a holder with the needle cannula in fixed relation to the holder. The holder is further dimensioned and configured for receiving and holding a sample collection tube in fluid flow communication with the needle assembly. The blood collection needle includes means for moving the needle assembly into the insertion configuration when a collection tube is installed in the holder and into the blunted configuration when the collection tube is removed from the holder.

The means for moving the needle assembly may comprise a mechanism comprising an actuator member configured and situated for engaging the blunting member, a transmitter member situated to engage a sample collection tube as it is installed in the holder, and a reversing link member that engages the actuator member and the transmitter member and that causes the actuator to move in an opposite direction from that of the transmitter member as described elsewhere herein. Optionally, there may be a biasing member positioned to be tensioned against the transmitter member when a collection tube is installed in the holder to bias the mechanism to the blunted configuration.

Optionally, any of the foregoing embodiments may further comprise locking means for locking the needle assembly in the blunted configuration. One such locking means may comprise a resilient detent mounted on one of the needle and the blunting member and a notch in the other, wherein the needle assembly is configured so that the detent engages the groove when the device is in the blunted configuration. Preferably, one of the actuator member, the transmitter member and the reversing link member is configured to disengage the detent from the notch in response to the movement of the actuator member towards the insertion configuration.

The present invention also relates to a method for taking at least one blood sample. The method comprises (a) inserting a needle cannula into a patient's tissue, (b) disposing a first sample collection tube in fluid flow communication with the needle to deliver a sample of blood into the tube, and (c) removing the first tube from the needle after a sample is delivered thereto and blunting the needle as the tube is being removed.

Optionally, step (b) may comprise inserting the tube in a holder for the needle and engaging and moving a transmitter in the holder with the tube, and step (c) may comprise withdrawing the tube from the holder.

The method may further comprise (d) disposing at least one subsequent sample collection tube in fluid flow communication with the needle and sharpening the needle and then, after a sample is delivered into the subsequent tube, (e) withdrawing the tube and blunting the needle.

Further details concerning the invention are described below with reference to the appended Figures.

BRIEF DESCRIPTION OF THE DRAWINGS

FIGS. 4A and 4B are views similar to FIG. 3 of the device of FIG. 3 in the insertion and blunted configurations, respectively;

FIGS. 8A and 8B are schematic cross-sectional views of a passive blood collection needle comprising the elements shown in FIGS. 5A, 6 and 7A, in the blunt and insertion configurations, respectively, with the needle assembly omitted to clarify the drawing;

DETAILED DESCRIPTION OF THE INVENTION AND PREFERRED EMBODIMENTS THEREOF

The present invention relates to a holder for a blood collection needle having a movable blunting member. The holder has a mechanism for deploying a blunting member upon withdrawal of a blood collection tube from the tube holder, to blunt the venipuncture needle and so safeguard the patient and the technician from inadvertent needle sticks. The mechanism may retract the blunting member to re-sharpen the venipuncture needle when a subsequent collection tube is inserted into the holder. The blunting mechanism is responsive to the insertion and withdrawal of the blood collection tube to retract and deploy the blunting member accordingly. One basic and novel feature of the present invention is that the blunting mechanism allows the user to blunt and, optionally, re-sharpen, the venipuncture needle without requiring manipulation of the collection tube or the needle holder other than that normally performed for conventional blood collection needle systems, as described above. For example, it is not necessary to manipulate the blunting member in any manner other than by the insertion or withdrawal of the sample tube to engage or disengage the filling needle. Four types of blunting mechanisms are disclosed: a rack and pinion arrangement; a cylindrical cam arrangement; a lever arrangement; and a pliable, resilient strap.

Also disclosed is a safety needle assembly comprising a needle cannula mounted in a needle hub combined with a blunting member mounted in a shuttle. The blunting member is designed to be received within the needle cannula and the shuttle is configured to be received within the needle hub. A locking mechanism comprising a detent resiliently mounted on the shuttle is configured to releasably engage locking apertures in the needle hub. The locking mechanism and the blunting mechanism may be used together by configuring the blunting mechanisms to release the detent from the locking apertures when the needle assembly is installed in the needle holder.

Figure 1A:
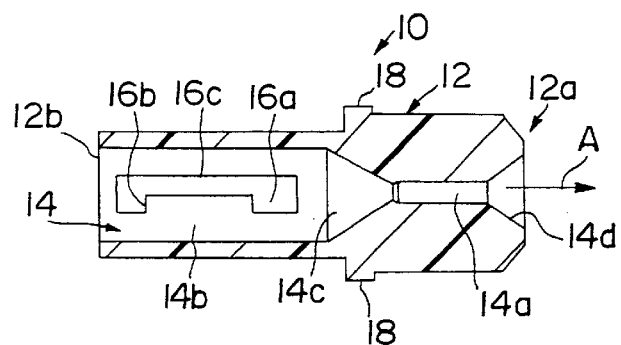
FIG. 1A is a cross-sectional view of a needle hub for holding a needle cannula in a blood collection device.

FIG. 1A shows a needle hub 10 that comprises a generally cylindrical body 12 having a longitudinal axis A, a first end 12a and a second end 12b. Needle hub 10 also comprises a circumferential locking flange 18 and at least one locking spline 20 (FIG. 1D) by which needle hub 10 can be secured in a needle holder, as described below. The interior of needle hub 10 comprises a hub passageway 14 extending therethrough. The shuttle portion 14b of passageway 14 (generally between second end 12b and flange 18) is dimensioned and configured to slidably receive a shuttle (FIG. 1B) therein. Body 12 defines two locking notches 16a and 16b and a channel 16c formed together as an aperture through the cylindrical wall of body 12. The mounting portion 14a of passageway 14 (generally between flange 18 and first end 12a) is dimensioned and configured to receive a needle cannula in the forward end thereof. The funnel-like insertion regions 14c and 14d at the ends of mounting portion 14a of passageway 14 converge from the shuttle portion 14b and the first end of hub 10, respectively, and facilitate the insertion therein of a blunting member and a needle cannula in assembly steps described below.

Figure 1B:
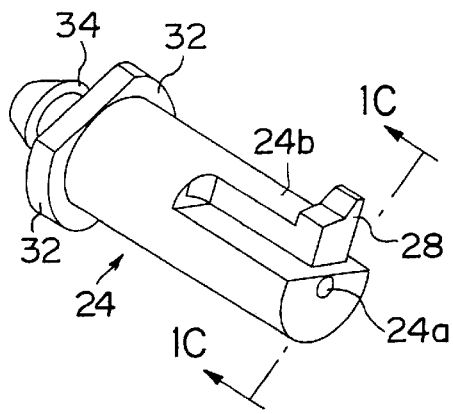
FIG. 1B is a perspective view of a blunting member shuttle intended for use with the needle hub of FIG. 1A.
Figure 1C:
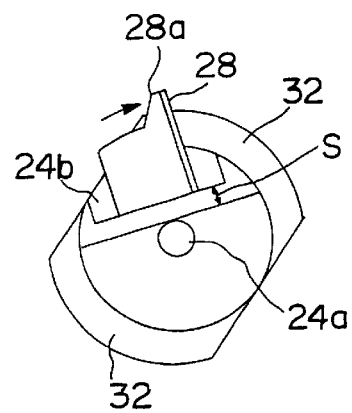
FIG. 1C is a view of the shuttle of FIG. 1B taken along line 1C—1C.

FIG. 1B shows a blunting member shuttle 24 which has a generally cylindrical body that is dimensioned and configured to be slidably received within the shuttle portion 14b of passageway 14 of hub 10, as will be described below. Shuttle 24 defines a central axial passageway 24a therethrough within which may be mounted a blunting member. Shuttle 24 comprises a detent 28 that is mounted on the end of a resilient arm 24b. Resilient arm 24b suspends detent 28 at a stand-off from the remainder of the shuttle body, indicated as stand-off S in the end view of FIG. 1C. As is evident from FIG. 1C, detent 28 has a protruding surface 28a that is disposed obliquely relative to the cylindrical periphery of shuttle 24. Therefore, a force applied upon surface 28a substantially along a tangent to the shuttle body (or parallel to such a tangent) can drive detent 28 in a radial direction (towards passageway 24a), narrowing stand-off S by flexing arm 24b.

Shuttle 24 comprises shuttle flanges 32 that permit shuttle 24 to engage another structure, as described below. Shuttle 24 also defines a boot barb 34 on which a self-sealing boot for sealing the sharpened insertion end 26b of blunting member cannula 26 may be anchored, as is well-known in the art.

Figure 1D:
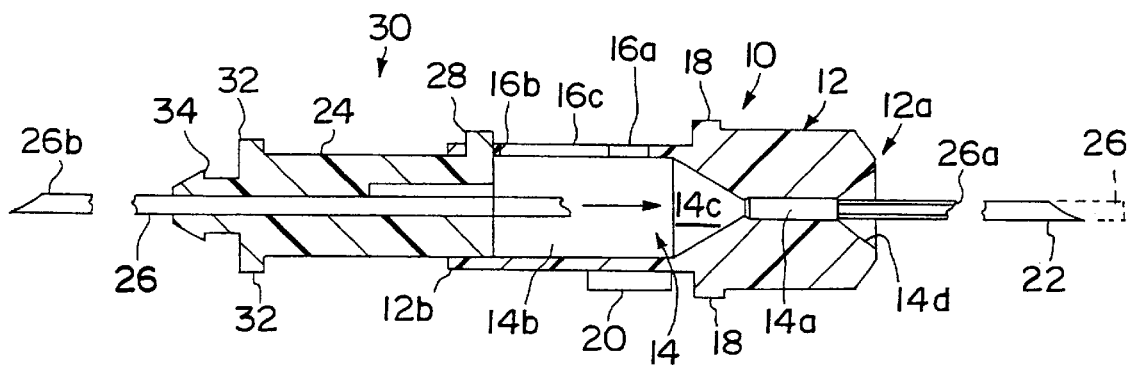
FIG. 1D is a cross-sectional view of a safety needle assembly comprising the hub and shuttle of FIGS. 1A and 1B with a needle cannula and blunting cannula secured therein.

FIG. 1D shows a safety needle assembly 30 that comprises needle hub 10, a hollow needle cannula 22 mounted therein, shuttle 24 and a hollow second cannula 26 mounted therein. Needle cannula 22 has a blunt proximal end that is inserted into the first end 12a of hub 10 and is secured therein by means of adhesive (not shown). The distal end of needle cannula 22 comprises a puncture tip. Passageway 14 defines a proximal insertion region 14d that converges rearward from first end 12a and thus facilitates the insertion of the blunt end of needle cannula 22 into passageway 14. The shuttle portion 14b of passageway 14 is dimensioned and configured to slidably receive shuttle 24 therein. A portion of second cannula 26 extends forward from shuttle 24 through passageway 14 and into needle cannula 22, within which it is telescopically disposed and wherein it terminates at a first, blunt end. The forward extending portion of second cannula 26 is referred to herein as the blunting member 26a. Second cannula 26 and needle cannula 22 cooperate to form a fluid flow passageway that extends through both of them. Thus, the blunting member 26a and the needle cannula 22 are disposed telescopically one within the other without obstructing flow through the needle passageway. Preferably, insertion region 14c converges to a diameter that is smaller than the internal diameter of needle cannula 22 and it is aligned therewith so that it provides a stop for the insertion of needle cannula 22 into body 12 as well as guiding blunting member 26a of blunting member cannula 26 into the proximal end of needle cannula 22. Second cannula 26 also extends rearward from shuttle 24, terminating at a second, sharp end (sometimes referred to herein as a "filling needle") for puncturing the seal on a collection tube and for providing a conduit to establish fluid flow communication between the collection tube and needle cannula 22, as will be described below. Second cannula 26 is securely mounted within shuttle 24 so that it moves with shuttle 24.

Detent 28 on shuttle 24 is dimensioned and configured to protrude through, and to be secured within, locking notches 16b and 16a, to secure the relative positions of shuttle 24 and needle hub 10. FIG. 1D shows needle assembly 30 in an insertion configuration (sometimes referred to herein as the "sharp configuration"), in which shuttle 24 is in a retracted position in hub 10. As shown, assembly 30 is locked in the sharp configuration by the engagement of detent 28 in rear locking notch 16b. Pressing detent 28 into passageway 14 disengages the detent from notch 16b so that shuttle 24 may be advanced within passageway 14. Detent 28 can slide along channel 16c until it engages forward locking notch 16a, thus securing shuttle 24 in an advanced or extended position within needle hub 10, resulting in a blunted configuration in which the blunt end of blunting member 26a protrudes beyond the sharp tip of needle cannula 22 (as indicated in dotted outline), blunting the needle assembly.

Figure 2:
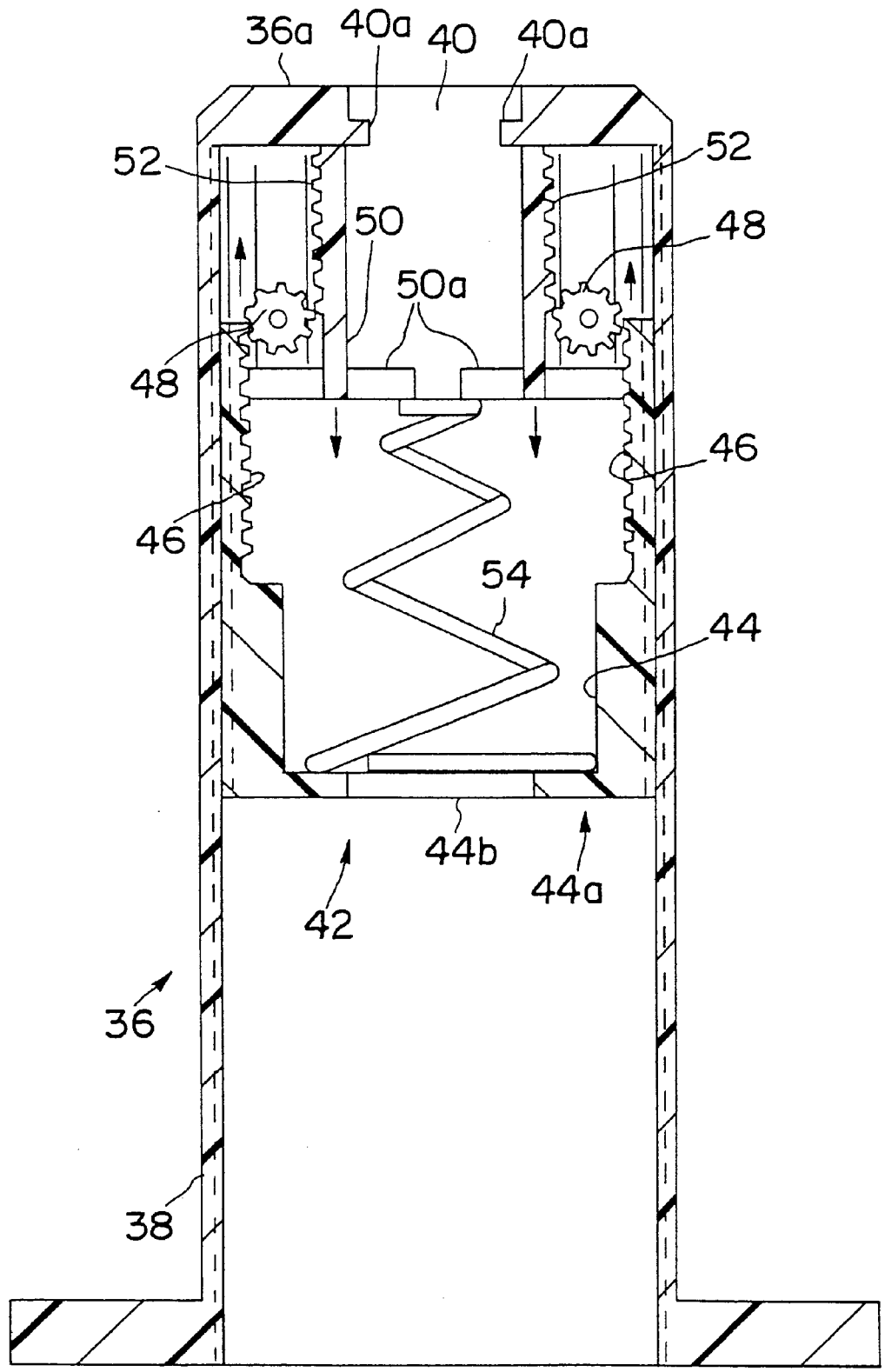
FIG. 2 is a cross-sectional view of a collection tube holder and a blunting mechanism for use with the present invention.

One embodiment of a needle assembly holder in accordance with the present invention is shown in FIG. 2. Holder 36 comprises a cylindrical shell 38 that defines a needle aperture 40 at its forward end. Aperture 40 is dimensioned and configured to receive a needle assembly comprising a needle cannula and a blunting member that are telescopically and movably disposed one within the other, such as needle assembly (FIG. 1D). An annular flange 40a protrudes into aperture 40 and defines notches (not shown) that are sized to allow spline 20 and detent 28 to pass therethrough as needle hub 10 is inserted into aperture 40. Flange 40a, however, is dimensioned and configured to engage hub flange 18 of needle assembly 30 (FIG. 1D). Flange 40a may be configured to be received in a friction fit between flanges 18 and spline 20 (FIG. 1D) when hub 10 is inserted into aperture 40 as far as flanges 18 and 40a will permit and then rotated to move spline 20 out of alignment with the notch in flange 40a. A stop lug (not shown) is positioned in aperture 40 to engage spline 20 upon such rotation and thus limit the rotation to a suitable turn, e.g., 45 degrees. Needle assembly 30 may thus be mounted in holder shell 38.

Shell 38 contains a mechanism 42. Mechanism 42 comprises a transmitting sleeve 44 comprising racks 46 which, in the illustrated embodiment, comprise toothed splines. Mechanism 42 further comprises pinions 48 which, in the illustrated embodiment, comprise toothed gears, and an actuator ferrule 50 comprising racks 52. Mechanism 42 also includes a spring 54. Pinions 48 engage racks 46 and 52 and thus serve as a link between them. In this embodiment and in the others described herein, the link member and its manner of connection to the transmitter, to the shell and to the actuator serve as means for moving the actuator in the holder in an opposite direction from that of the transmitter. Transmitting sleeve 44 is slidably disposed in the interior of shell 38 and racks 46, which are preferably diametrically opposed from one another in shell 38 are slidably disposed in axial grooves in the interior wall of shell 38. Transmitting sleeve 44 has at its coupling end 44a an access aperture 44b. Coupling end 44a is dimensioned and configured to engage the filling end of a conventional collection tube and aperture 44b permits the sharp end of a filling needle such as the end of cannula 26 (FIG. 1D) to protrude therethrough into a collection tube. Pinions 48 are mounted in shell 38 and are dimensioned and configured to rotatably engage racks 46 of transmitting sleeve 44. FIG. 2 shows mechanism 42 in a deployed configuration, i.e., a configuration in which actuator ferrule 50 is positioned forward in shell 38, from where it can be retracted (moved downward, as sensed in the Figure), as will be described herein. (This position is referred to as "deployed". When the actuator ferrule engages a blunting member in this position, the blunting member is extended, to blunt the needle, as will be described herein.) Spring 54, between end cap 50a of actuator ferrule 50 and transmitting sleeve 44, is lightly compressed to bias the mechanism into the illustrated pre-filling position and is situated so that it is tensioned against the transmitting sleeve 44 when transmitting sleeve 44 and actuator ferrule 50 approach each other as described below. Actuator ferrule 50 is disposed within shell 38 and comprises a pair of racks 52 that engage pinions 48. The interior of ferrule 50 is dimensioned and configured to permit the insertion and rotation of needle assembly 30 therein as is necessary to mount needle assembly 30 in shell 38, without depressing detent 28 (FIG. 1D). For example, ferrule 50 may have an L-shaped groove on its interior surface, with detent 28 moving in an axial or longitudinal leg of the groove as needle assembly 30 is inserted into shell 38. Detent 28 may then move in a circumferential leg of the groove when needle assembly 30 is rotated in aperture 40. Alternatively, ferrule 50 may have an internal lug or fillet positioned to engage detent 28 only after needle assembly 30 is mounted in shell 38 and ferrule 50 is moved rearward.

Analogously to the interrelation on needle assembly 30 (FIG. 1D) of spline 20 and annular flange 40a, the shuttle flanges 32 on shuttle 24 are eccentrically configured about the longitudinal axis of the device, and actuator ferrule 50 forms a cap aperture in cap 50a that is configured to align with flanges 32 and permit them to pass therethrough upon initial insertion of needle assembly 30 into shell 38. Spring 54 is configured so that when the shuttle flanges 32 pass through the aperture in cap 50a they engage spring 54. The rotation of needle assembly 30 that mounts the assembly in shell 38 also turns flanges 32 out of alignment with the aperture so that cap 50a can thereafter engage the flanges 32 under the force of spring 54. Actuator ferrule 50 can thus engage blunting member 26a, via shuttle 24.

Mechanism 42 is dimensioned and configured so when transmitting sleeve 44 is moved forward within shell 38 (e.g., as a result of the insertion of a collection tube), actuator ferrule 50 moves in the reverse direction, away from forward end 36a, under the operation of pinions 48. Mechanism 42 thus moves from the pre-filling configuration shown in FIG. 3 to a filling configuration. Such movement also imposes further tension or compressive force on spring 54.

Figure 3:
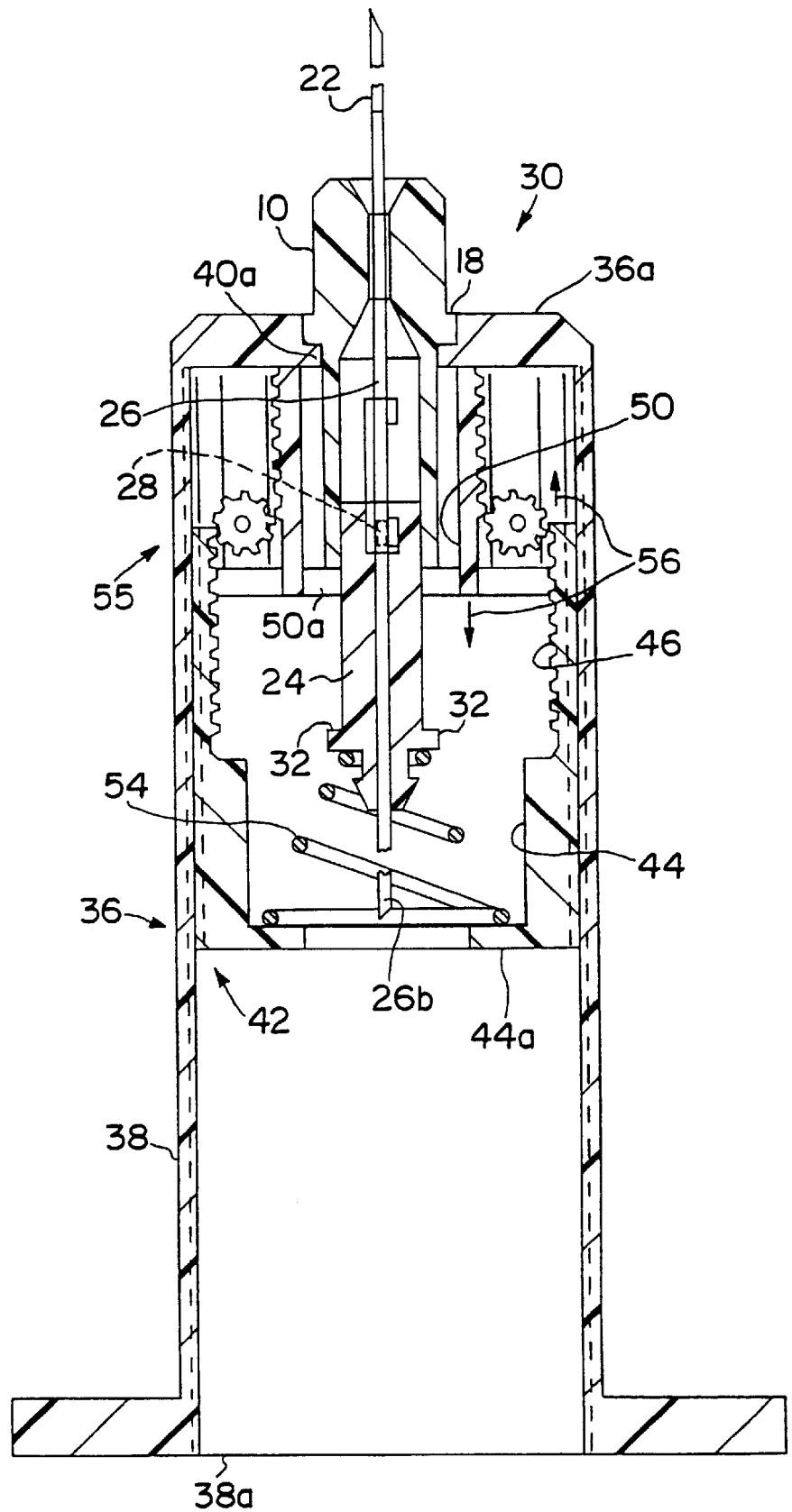
FIG. 3 is a cross-sectional view of a passive blood collection needle in accordance with a particular embodiment of the present invention, comprising the holder and blunting mechanism of FIG. 2 and the needle assembly of FIG. 1D.

The fully assembled blood collection needle 55 is shown in FIG. 3 with needle assembly 30 mounted in aperture 40 (FIG. 2) with the needle cannula in fixed relation to the holder because of the engagement of annular flange 40a (FIG. 2) with flange 18 (FIG. 1D) and spline 20 (FIG. 1D, not seen in FIG. 3). Collection needle 55 is in an initial, pre-filling configuration in which needle assembly 30 is in a sharpened configuration even though actuator ferrule 50 is in a deployed position, because shuttle 24 on blunting member 26a has not yet engaged actuator ferrule 50. Note that shuttle flanges 32 of needle assembly 30 protrude beyond end cap 50a (FIG. 2) of ferrule 50 and compress spring 54. Shuttle 24 resists being moved by spring 54 forward into hub 10 because detent 28 is locked in notch 16b (FIG. 1A), leaving needle assembly 30 locked in the sharp configuration, ready for venipuncture.

Figure 4B:
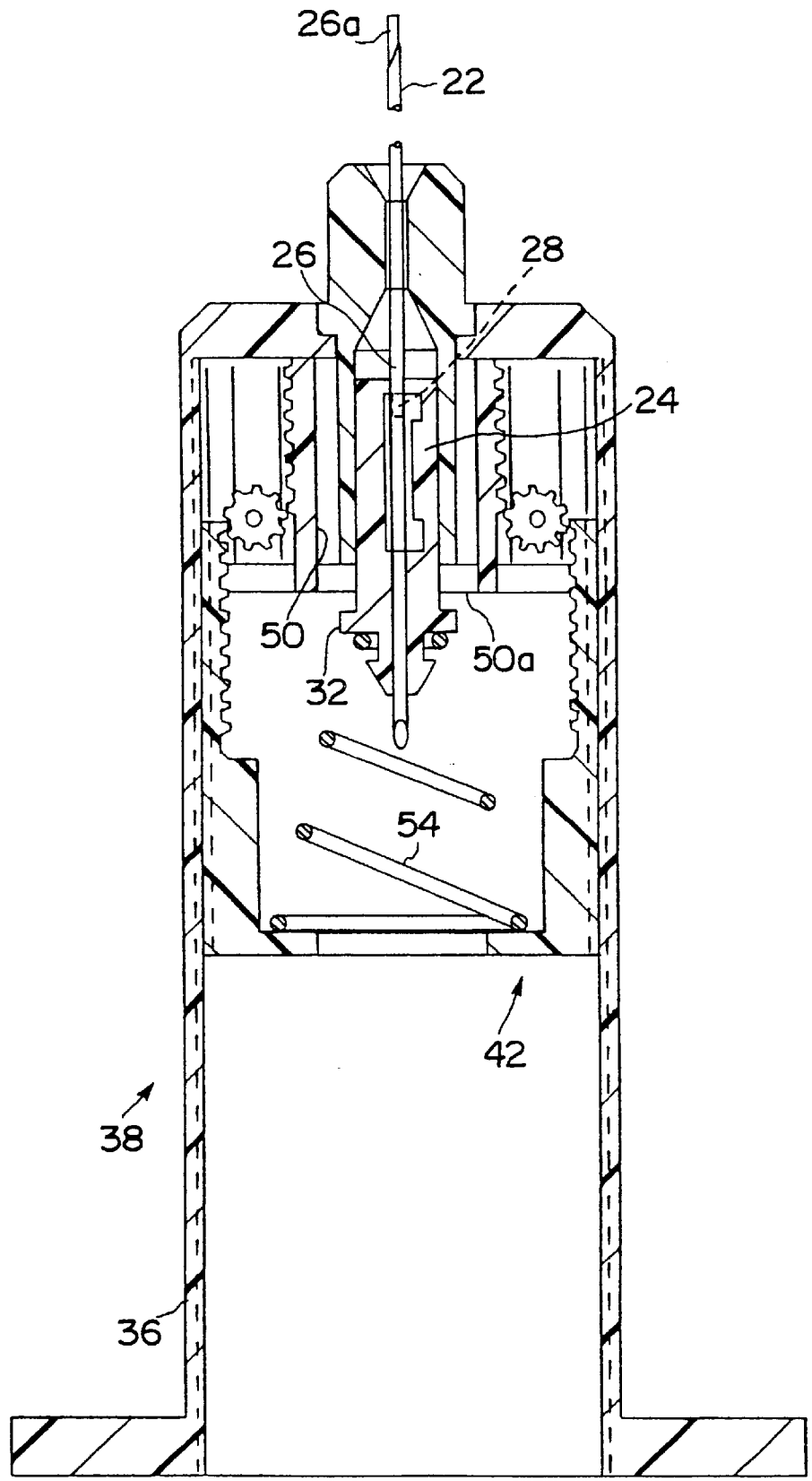

To prepare blood collection needle 55 for use, a technician will typically install needle assembly 30 in holder 36 as shown in FIG. 3, and then remove from needle cannula 22 a protective sheath (not shown) and insert needle cannula 22 into a patient's vein. Then, the technician will take a conventional collection tube 56a (FIG. 4A) and insert the capped end thereof into the open end 38a of shell 38 with sufficient force to assure that filling needle 26b punctures the seal cap 56b on the collection tube, thus establishing flow communication between the collection tube and the needle assembly. This action will impose sufficient force on coupling end 44a to drive transmitting sleeve 44 forward in needle holder 36 (upward as sensed in FIG. 3) and will compress spring 54. The operation of mechanism 42 will transfer the forward motion of transmitting sleeve 44 into rearward movement of actuator ferrule 50 indicated by arrows 56 (downward, as sensed in FIG. 3), under the operation of pinions 48. Thus, mechanism 42 causes actuator ferrule 50 to move in a direction opposite from that of transmitting sleeve 44. The interior of ferrule 50 is configured so that such rearward movement causes it to depress detent 28 and thus unlock the needle assembly. Shuttle flanges 32 then bear on end cap 50a under the force of spring 54. This motion will conclude with mechanism 42 in the retracted configuration shown in FIG. 4A, in which actuator ferrule 50 and shuttle 24 are in their retracted positions due to the advancement of transmitting sleeve 44, leaving needle assembly 30 in the sharpened configuration. With the forward end of needle cannula 22 in a patient's vein and the filling needle 26b of second cannula 26 in an evacuated collection tube, blood will flow through the fluid flow passageway of the device to fill the collection tube. It is advantageous for the needle assembly 30 to be sharp while the sample tube is filling because the filling process may be interrupted if the needle is jostled or obstructed and it may be necessary for the technician to re-position the needle in the vein; this is better accomplished with a sharp needle than a blunt one. Upon subsequent withdrawal of the collection tube 56a from shell 38, transmitting sleeve 44 will move according to the bias of spring 54 in the direction of arrows 58. The operation of the mechanism 42 will, accordingly, move actuator ferrule 50 in the opposite direction, towards its forward (upward), pre-filling position. Shuttle 24 will also move forward (upward, as sensed in the Figure) with ferrule 50, under the impetus of spring 54, so that the blunt end 26a of the blunting cannula is extended beyond the tip of needle cannula 22, thus blunting the device. Shuttle 24 locks in the forward position with the blunt end 26a of blunting member cannula 26 extending beyond the puncture tip of needle cannula 22 before actuator ferrule 50 stops its forward movement. The additional forward movement of actuator ferrule 50 relative to shuttle 24 allows the internal fillet or groove that previously unlocked the needle assembly to disengage from the locking detent. Accordingly, detent 28 can engage locking notch 16a to lock needle assembly 30 in the blunted configuration. The additional forward movement of ferrule 50 also causes end cap 50a to disengage from shuttle flanges 32. Mechanism 42 comes to rest in the deployed configuration shown in FIG. 4B. Subsequent insertion of another collection tube will cause the actuator ferrule 50 to move rearward again, unlocking shuttle 24 and then engaging shuttle flanges 32 to return to the sharpened configuration shown in FIG. 4A, and removal of the tube thereafter will once again return the device to the blunted configuration of FIG. 4B. Thus, after the initial insertion of a sample tube, mechanism 42 serves to move actuator ferrule 50 and the blunting member 26a in a direction contrary to that of the sample tube and transmitting sleeve 44 in the holder shell. Such motion is illustrated as changes between the configurations of FIGS. 4A and 4B.

In an alternative embodiment, actuator ferrule 50 may carry locking flanges disposed about the central aperture of end cap 50a (FIG. 2). Such locking flanges may be configured to engage shuttle flanges 32 (FIG. 1D) when the first insertion of a blood collection tube moves actuator ferrule 50 rearward from the initial configuration (FIG. 3) to the filling configuration shown in FIG. 4A.

In an alternative aspect of this invention, a mechanism in accordance with the present invention may incorporate a cam and follower arrangement instead of a rack and pinion arrangement. In such an embodiment, a rotating cylindrical cam (referred to herein as a "rotator") will be disposed within the cylindrical body of the needle holder carrying the self-blunting needle assembly. An actuator structure (or "inner sleeve") that engages the blunting member will follow the cam surface of the rotator. When the rotator rotates within the needle holder, the actuator follows by imposing a corresponding axial motion on the blunting member in accordance with the direction of rotation of the rotator. The device is configured so that the forward insertion of a sample tube into the needle holder rotates the rotator in a direction that causes the actuator to retract (rearward) within the needle holder. The rotating cam embodiment of the present invention, like the rack and pinion embodiment, creates contrary motion between the blunting member and the sample tube inserted into the holder with each insertion and withdrawal of a tube, except for the first time a collection tube is inserted into the holder. Such a device can employ the safety needle assembly 30 of FIG. 1B, as described below.

Figure 5A:
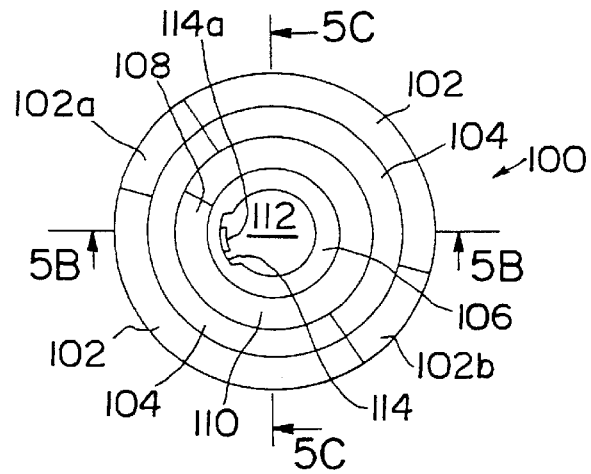
FIG. 5A is a schematic plan view of a rotator element for use in a blunting mechanism in accordance with another embodiment of the present invention.
Figure 5B:
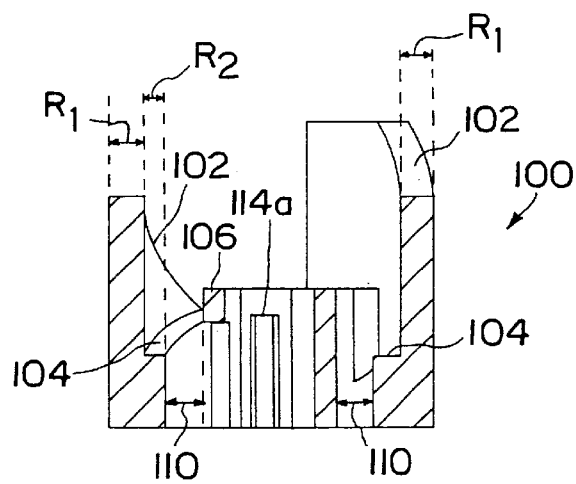
FIG. 5B is a cross-sectional view of the element of FIG. 5A taken along line 5B—5B.
Figure 5C:
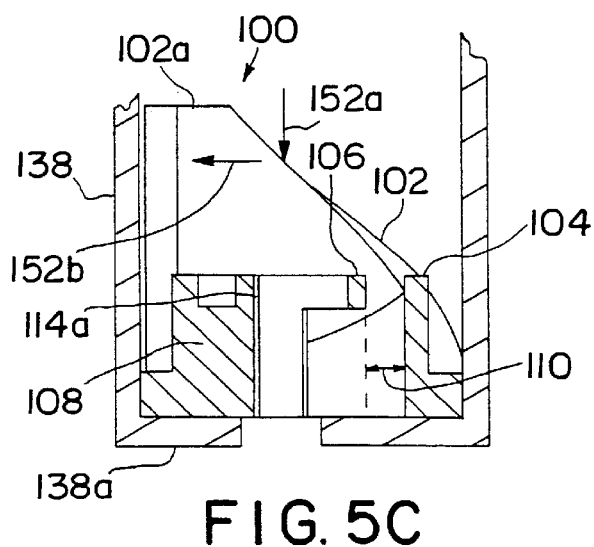
FIG. 5C is a cross-sectional view of the element of FIG. 5A taken along line 5C—5C.

FIGS. 5A, 5B and 5C provide related views of a cylindrical cam or "rotator" 100 for use in one embodiment of the present invention. In the plan view of FIG. 5A, rotator 100 is seen to have a round periphery, thus allowing for coaxial rotation within a cylindrical needle holder. Rotator 100 has three principal concentric annular segments: at least one following surface 102, at least one driving surface 104 and a central collet 106. Following surfaces 102 are disposed in the circumferential, outermost annular segment of rotator 100, which includes a flat upper surface 102a and a flat lower surface 102b. Driving surfaces 104 are concentrically contiguous with following surfaces 102. Proceeding radially inward, the next annular segment of rotator 100 is collet 106, which is physically connected to surfaces 102 and 104 by a bridge 108. Bridge 108 spans a region between collet 106 and driving surfaces 104 that is occupied principally by a curvate gap 110. The interior region 112 of collet 106 defines a recess 114 within which is disposed an unlocking fillet 114a. Fillet 114a is better viewed in FIG. 5B, which also shows that the following surfaces 102 occupy a first annular region R1 and driving surfaces 104 occupy the contiguous annular region R2.

As is evident from FIG. 5C, rotator 100 can be disposed within the generally cylindrical shell 138 of a needle holder, rotatably resting on the bottom shoulder 138a of shell 138. So disposed, the impingement of an axial force as indicated, e.g., by arrow 152a, on following surface 102 will cause rotator 100 to rotate in the direction of arrow 152b. If the structure imposing the force at arrow 152a is not permitted rotational movement as it bears on surface 102, it will move downward (axially) as rotator 100 rotates. Since driving surfaces 104 slope in a helical direction opposite from that of following surfaces 102, a structure that is slidably disposed on surface 104 and that is constrained against rotation will move upward on the contrary incline of driving surface 104 as the structure on surface 102 moves downward, as will be discussed further below.

Figure 6:
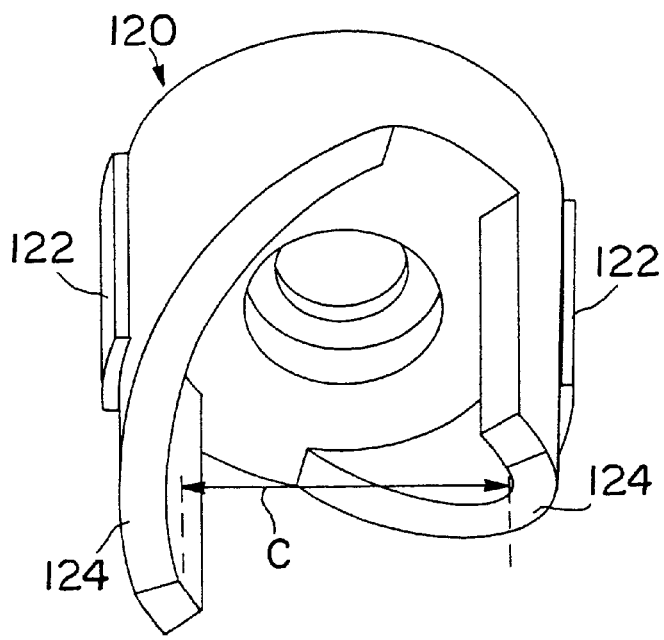
FIG. 6 is an exploded perspective view of a transmitter element and an actuator element for use with the rotator element of FIG. 5A in a blunting mechanism in accordance with the present invention.
Figure 6:
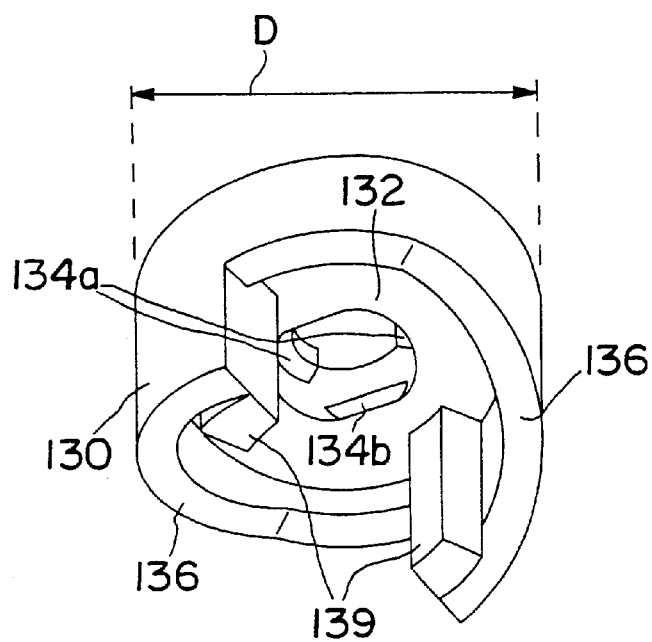

A force transmitter and cam follower/actuator that bear on surfaces 102 and 104, for driving and following rotator 100, are shown in an exploded coaxial relationship in FIG. 6. Transmitter 120 has a generally cylindrical configuration dimensioned to have the same outer diameter as rotator 100 so that the two can fit snugly in the same cylindrical needle holder shell. However, transmitter 120 also comprises guiding means for engaging the interior surface of the shell so that transmitter 120 will be inhibited against free rotational motion within the shell. Preferably, it will be constrained for axial motion within the shell. In the embodiment of FIG. 6, the guiding means of transmitter 120 comprises a pair of peripheral guiding fillets 122 that are dimensioned and configured to be slidably received within axially-extending grooves in the interior wall of the shell within which transmitter 120 is disposed. With the fillets 122 disposed in such grooves, transmitter 120 will be able to move axially, i.e., longitudinally, within the holder shell, but will not be able to rotate therein. Transmitter 120 comprises a pair of driving surfaces 124 that are dimensioned and configured to engage following surfaces 102 of rotator 100 in annular region R1, within which they define a cylindrical receiving region C.

Also shown in FIG. 6 is actuator 130 which has a cylindrical outer configuration having a diameter D dimensioned to be received within receiving region C of transmitter 120. Actuator 130 has a central aperture 132 into which locking tabs 134a, 134b extend, for engaging the shuttle flanges 32 of needle assembly 30 (FIG. 1B). Actuator 130 defines a pair of following surfaces 136 that are dimensioned and configured for complementary engagement with driving surfaces 104 in annular region R2 of rotator 100. However, actuator 130 is constrained against rotational movement by the engagement of internal lugs 139 with a pair of posts (not shown) that extend upward from bottom shoulder 138a of shell 138 and which protrude through rotator 100 via gap 110.

Figure 7A:
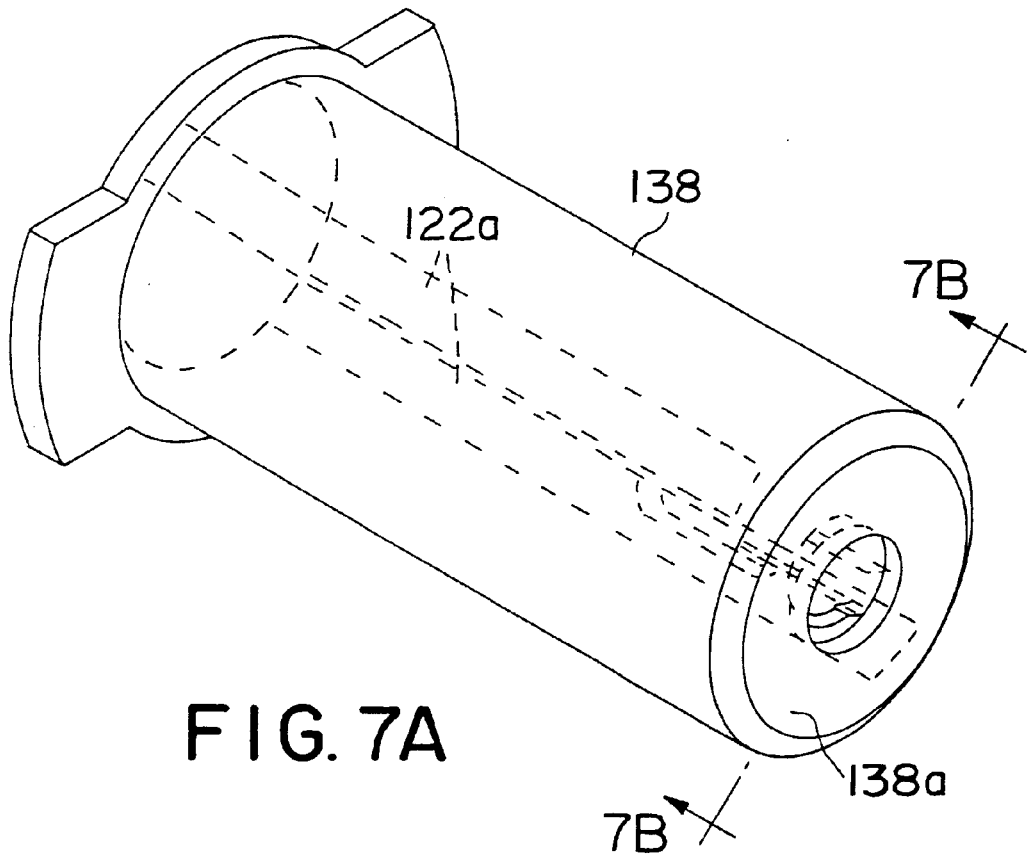
FIG. 7A is a perspective view of a sample tube holder for use with the elements shown in FIGS. 5A and 6.
Figure 7B:
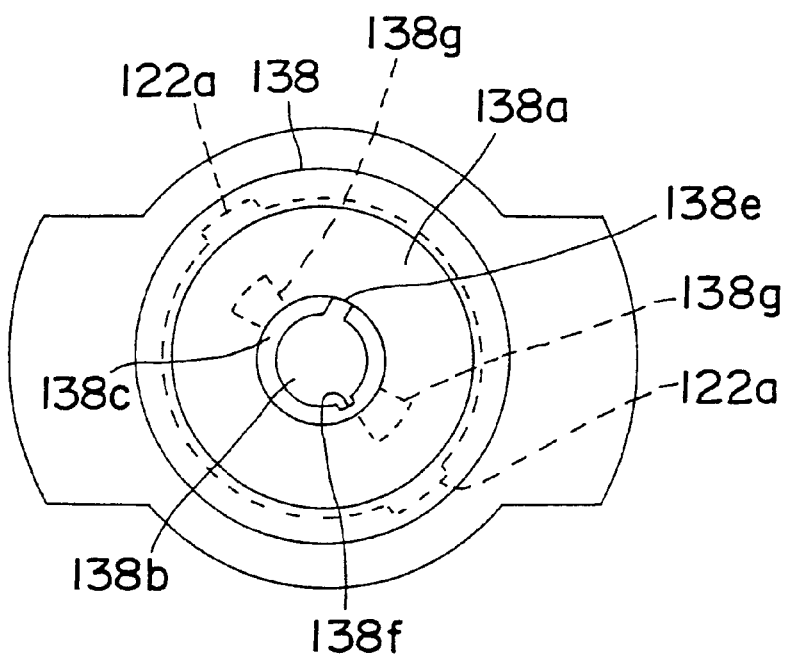
FIG. 7B is a view of the holder of FIG. 7A taken along line 7B—7B.

FIG. 7A provides a perspective view of a sample tube holder that may house a mechanism comprising the rotator 100, transmitter 120 and actuator 130 of FIGS. 5A, 5B, 5C and FIG. 6. The holder comprises a shell 138 having a longitudinal axis A and a shoulder 138a at its forward end. Shell 138 defines a pair of internally, axially disposed grooves 122a, shown in dotted outline. FIG. 7B provides an end view of shell 138, showing aperture 138b which is dimensioned and configured to receive safety needle assembly 30 of FIG. 1D. Aperture 138b is substantially circumscribed by a flange 138c that is dimensioned and configured to permit the blunting component and rearward portion of the needle hub therein, but to engage hub flanges 18 (FIG. 1D), leaving the forward end 12a of needle hub 12 extending forward from shoulder 138a. Notch 138e is configured to receive a locking spline 20 (FIG. 1D), and notch 138f is dimensioned and configured to allow the detent 28 (FIGS. 1C and 1D) to pass through aperture 138b to avoid unlocking the needle assembly as it is first being inserted into shell 138. After insertion of the needle assembly into the aperture, the needle assembly is rotated so that the locking spline and flanges 18 engage flange 138c. Also seen in FIG. 7B are two posts 138g that extend axially from shoulder 138a towards the rearward end of shell 138.

FIGS. 8A and 8B are cross-sectional schematic drawings that indicate the relative positions of the transmitter 120, rotator 100 and actuator 130 in two different configurations within shell 138. FIG. 8A depicts the holder mechanism in the deployed configuration. In this configuration, rotator 100 is rotatably situated within shell 138 and, because it is resting on shoulder 138a, it is constrained against forward axial movement. The transmitter 120 is disposed in shell 138 so that the lower (as sensed in FIG. 8A) portions of its helical driving surfaces 124 engage the upper portions of the following surfaces 102 of rotator 100. Transmitter 120 carries fillets 122 that engage grooves 122a in shell 138 and thus permit axial sliding motion of transmitter 120 in shell 138 but prevent rotational motion. Actuator 130 is disposed within the outermost annular region of rotator 100, with following surfaces 136 engaging driving surfaces 104. An internal post 138g extending from shell 138 through gap 110 (FIG. 5B) engages lug 139 to prevent actuator 130 from rotating within shell 138. A spring 154 is disposed axially between transmitter 120 and actuator 130.

When a forward (downward, as sensed in the Figure) force is imposed on bearing surface 120a of transmitter 120, e.g., by pressing a sample collection tube into shell 138, transmitter 120 moves downward, as indicated by arrow 156a and the spiraled driving surface 124 bears upon the complementary following surface 102 of rotator 100. Since transmitter 120 is constrained against rotation, transmitter 120 acts like a driving cam follower and the downward motion of transmitter 120 causes rotator 100 to rotate within shell 138. Such rotation of rotator 100 will cause driving surface 104 to impose a force upon following surface 136 of actuator 130. Since actuator 130 is constrained against rotational motion by the engagement of lugs 139 with the posts 138g extending upward from shoulder 138a, the force imposed by driving surface 104 will cause actuator 130 to move upwards (as indicated by arrow 156b). Thus, rotator 100 serves as a linking member that moves actuator 130 in a direction opposite from that of transmitter 120. The result of the downward axial motion of transmitter 120 is the retracted configuration depicted in FIG. 8B, which shows rotator 100 in a rotated position and actuator 130 in an elevated position relative to FIG. 8A.

As transmitter 120 and actuator 130 move towards each other from the pre-filling configuration of FIG. 8A to the filling configuration of FIG. 8B, they compress spring 154. The friction fit of a collection tube in shell 138 is sufficient to withstand the tendency of spring 154 to decompress and move transmitter 120 (and the collection tube pressing against it) upward. However, upon manual removal of the collection tube, spring 154 will drive transmitter 120 upward so that it remains in contact with the collection tube until it encounters a stop lug on the interior wall of shell 138, e.g., lug 122b in groove 122a. During the withdrawal process, the upward motion of transmitter 120 will tend to disengage driving surface 124 from following surface 120. However, the residual downward force imposed by spring 154 on actuator 130 will cause following surface 136 to bear on driving surface 104, to which rotator 100 will respond by rotating sleeve 138 until following surface 102 again engages driving surface 124. Further withdrawal of the collection tube will allow spring 154 to drive transmitter 120 still higher and actuator 130 still lower in shell 138, thus imposing further rotation on rotator 100 until the configuration of FIG. 8A is regained.

Figure 8C:
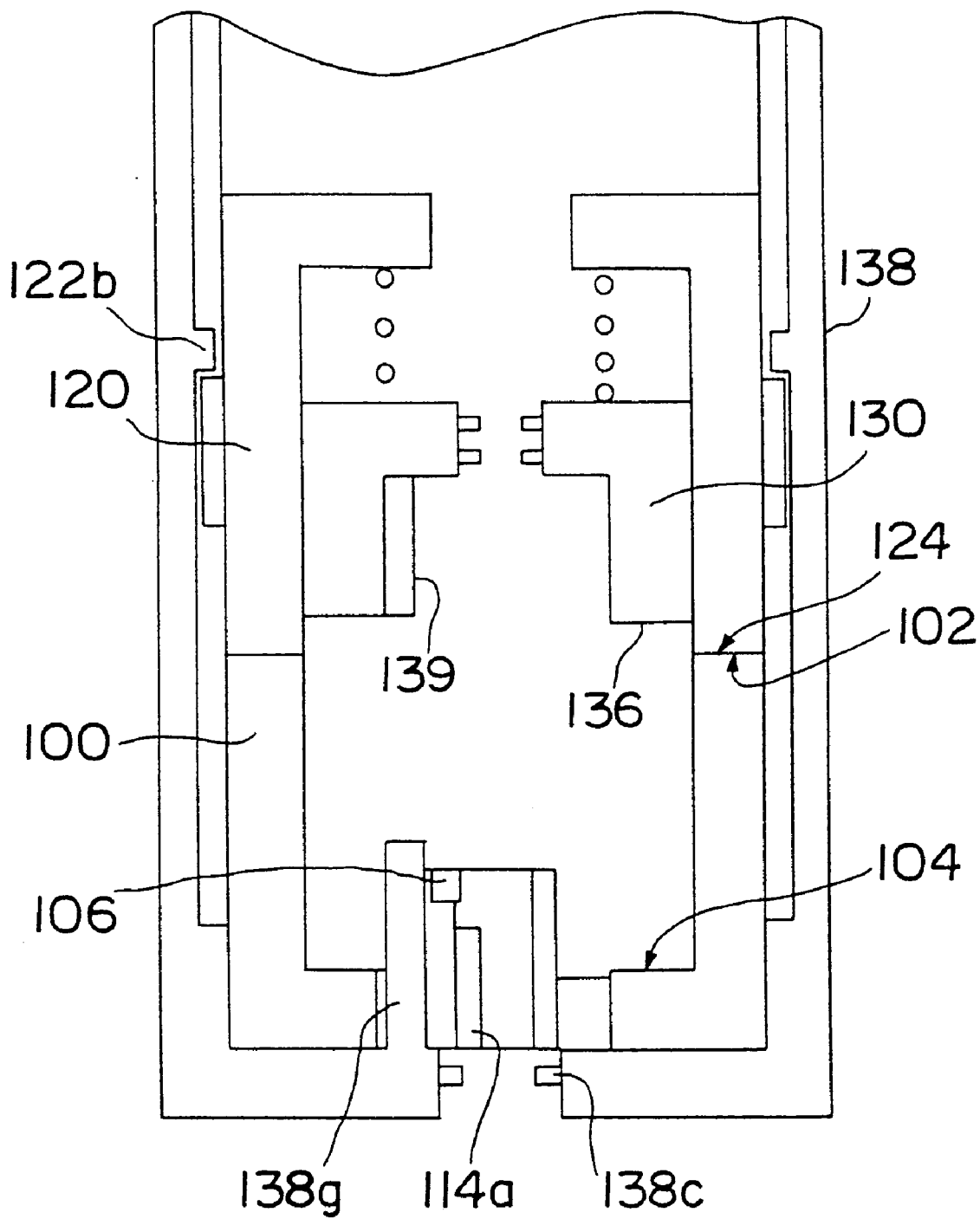
FIG. 8C is a view similar to FIGS. 8A and 8B of the blunting mechanism as it will be configured upon the initial installation of a locked needle assembly prior to insertion of a sample collection tube.

As with the rack and pinion embodiment of FIGS. 1 through 4B, the needle assembly 30 is first inserted into the shell 138 in the sharpened configuration (shown in FIG. 1D) with mechanism 142 in the deployed configuration of FIG. 8A. As needle assembly 30 is inserted into aperture 138b, detent 28 (FIG. 1D) passes through notch 138f (FIG. 7B) of shell 138, and then alongside fillet 114a (FIG. 5B). Locking spline 20 (FIG. 1D) passes through notch 138e (FIG. 7B), and hub flanges 18 (FIG. 1D) come to a stop against flange 138c (FIGS. 7B, 8A). The needle assembly is rotated to engage flange 138c between spline 20 and flanges 18, thus locking the needle in the holder. This rotation disposes detent 28 beside fillet 114a. Meanwhile, the shuttle flanges 32 bear against flanges 134a of actuator 130, pushing actuator 130 upward (as sensed in FIG. 8A) and lifting it off rotator 100 to the position shown in FIG. 8C. The rotation of needle assembly 30 that engages flange 138c also positions shuttle flanges 32 (FIGS. 1B, 1D) between actuator flanges 134a and 134b (FIG. 6). Transmitter 120 and rotator 100 are in a deployed configuration, but actuator 130 is retracted and the needle assembly is sharp.

When the first sample tube is inserted into holder shell 138, it bears on transmitter 120, which moves downward, causing rotator 100 to rotate. This makes fillet 114a swipe surface 28a (FIG. 1C) on detent 28 and unlock the needle assembly. Shuttle 24 then allows actuator 130 to move forward (downward as sensed in FIG. 8A), but only until its following surface 136 engages driving surface 104 of rotator 100. The apparatus is configured so that this occurs before the blunting member blunts the needle. The continued rotation of rotator 100 in response to the further insertion of the sample tube then moves actuator 130 back upwards. At the point of full insertion of the sample tube, the device reaches the retracted configuration of FIG. 8B, in which flanges 134b of actuator 130 hold shuttle 24 (not shown) in the retracted position, leaving the needle assembly in the sharpened configuration. Upon withdrawal of the sample tube, spring 154 drives the device back to the deployed configuration of FIG. 8A, and actuator 130 advances shuttle 24 forward, blunting the needle. Insertion of yet another collection tube will bring the device back to the sharpened configuration of FIG. 8B.

Figure 8D:
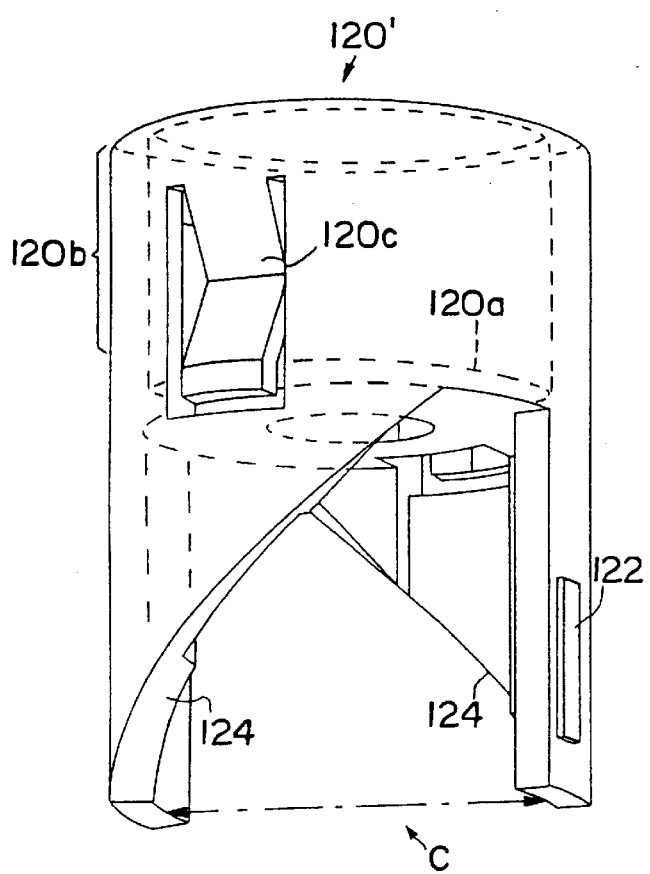
FIG. 8D is an elevation view of a transmitter member of a blunting mechanism according to yet another embodiment of this invention.
Figure 8E:
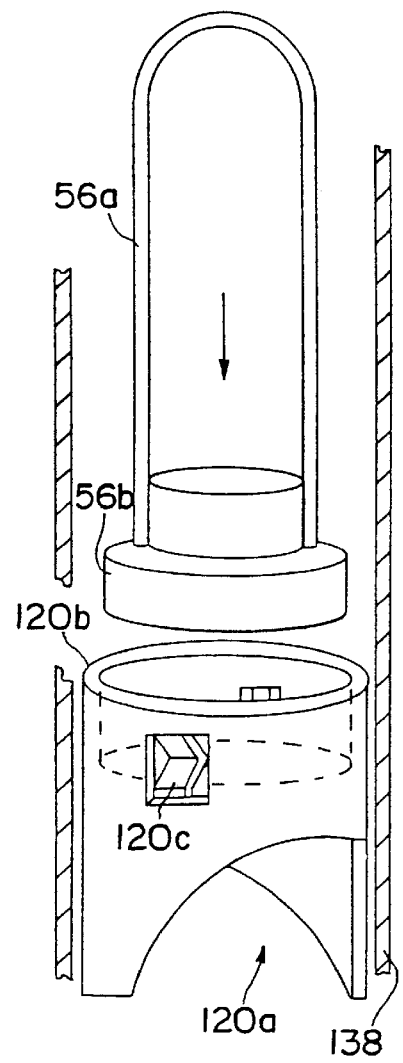
FIG. 8E is an elevation view of the transmitter of FIG. 8D together with a blood collection tube in a holder shell shown in cross section.

In accordance with another embodiment of the invention, the transmitter may be dimensioned and configured to engage the sample collection tube. For example, a transmitter 120' shown in FIG. 8D has a generally cylindrical configuration that defines a cylindrical receiving region C and driving surfaces 124 corresponding to those of transmitter 120 (FIG. 6). In addition, however, transmitter 120' comprises a receiving ferrule 120b that extends axially from bearing surface 120a in a direction opposite from driving surfaces 124. Receiving ferrule 120b defines an interior region that is dimensioned and configured to receive the seal cap on a conventional sample blood collection tube. In addition, receiving ferrule 120b carries a leaf spring 120c which may optionally be formed integrally therewith as shown in the Figure. Leaf spring 120c protrudes into the interior region of receiving ferrule 120b and it is configured so that it will be displaced by a sample collection tube inserted therein. As suggested in FIG. 8E, a collection tube such as blood collection tube 56a, which carries a seal cap 56b, may be inserted into the cylindrical holder 138 and thus into the receiving ferrule 120b of transmitter 120' therein. As this occurs, seal cap 56b will displace leaf spring 120c outwardly. Leaf spring 120c is configured so that such displacement causes it to bear against the interior of the holder shell, thus increasing the friction between transmitter 120' and the surrounding shell 138. This added friction helps keep tube 56a in place during the filling process despite the bias of spring 154.

Figure 9A:
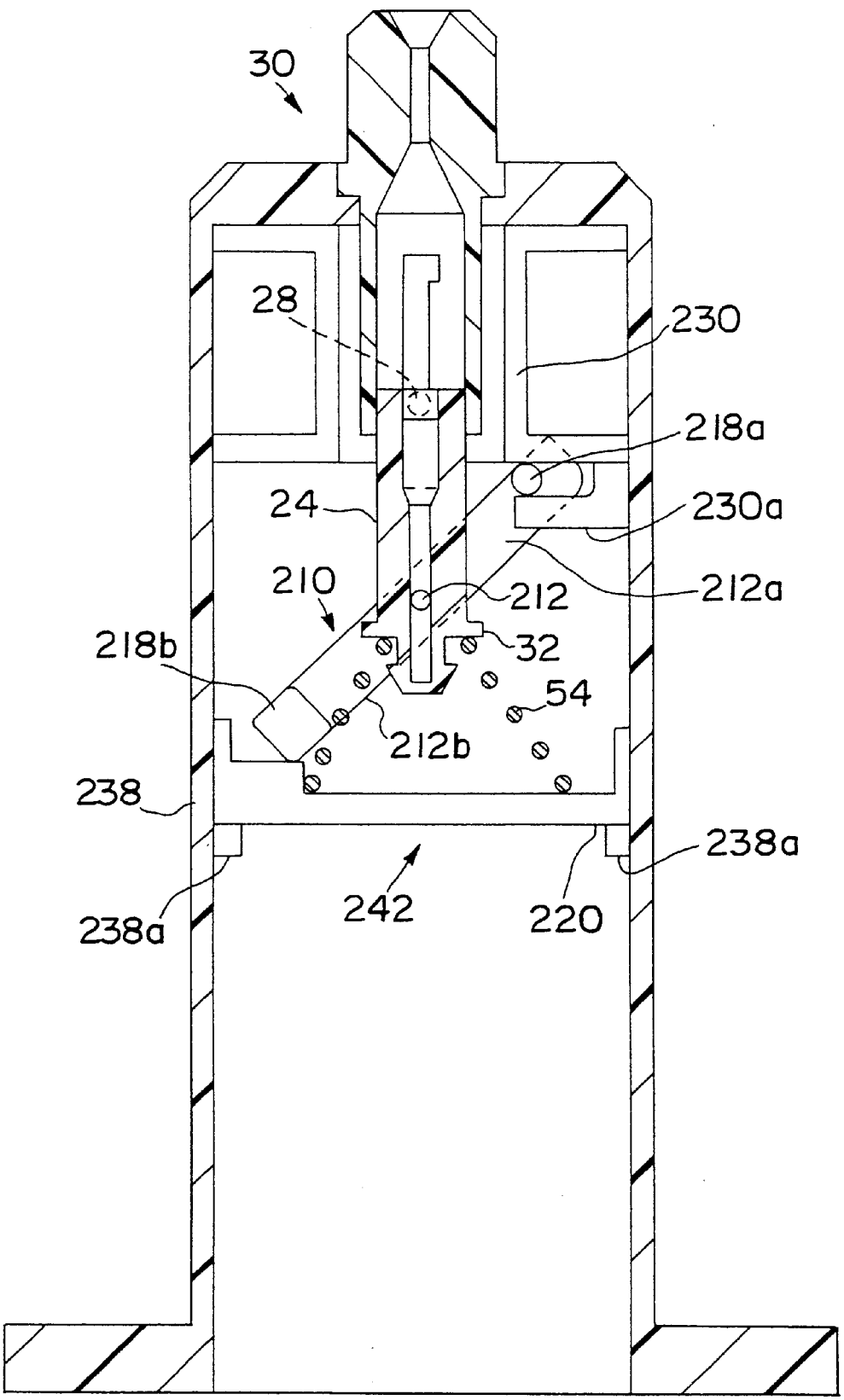
FIG. 9A is a cross-sectional schematic view of a blunting mechanism in a needle holder in accordance with still another embodiment of the present invention.
Figure 9B:
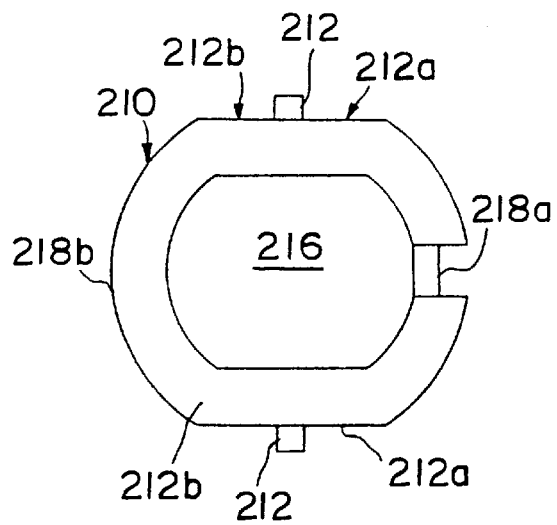
FIG. 9B is a plan view of ring lever 210 of FIG. 9A.

The embodiment of FIG. 9A provides a schematic illustration of a lever-based mechanism for the present invention. Mechanism 242 makes use of a ring lever 210, shown in plan view in FIG. 9B and in perspective view in FIG. 9C. Ring lever 210 is configured in the shape of a ring having a pair of fulcrum studs 212 extending outwardly and coaxially therefrom. Studs 212 define the fulcrum of lever ring 210 and divide ring 210 into two roughly semi-circular arms 212a and 212b that extend therefrom. As sensed in FIG. 9A, arm 212a extends upward (or forward) and comprises a pintle 218a for connecting to the actuator 230 in a hinge-like manner that permits pintle 218a to move radially so that ring lever 210 can pivot. Arm 212b extends downward (rearward) and comprises a bearing portion 218b for engaging the transmitter baffle 220 in a manner that allows movement corresponding to that of pintle 218a on actuator 230. The central region 216 (FIG. 9B) of ring 210 is configured to allow the blunting member and associated shuttle to pass therethrough.

When ring lever 210 is mounted by studs 212 for rotation about their axis 212a, a force applied to a non-axial point on ring 210, as indicated by the application of force F1 at a point diametrically opposite from pintle 218a, will produce a rotation about studs 212. As sensed in FIG. 9C, an upward motion of bearing portion 218b resulting from an upwardly-directed force F1 will produce a contrary, downward motion of pintle 218a, as indicated by arrow F2.

In accordance with this aspect of the invention, ring lever 210 is mounted inside holder shell 238 with studs 212 rotatably disposed at right angles to the longitudinal axis of the shell. Pintle 218a is connected to an actuator frame 230 by engaging lift arm 230a connected thereto. A transmitter baffle 220 is mounted within shell 38 for axial sliding motion between a stop member 238a on shell 238 and frame 230. Transmitter baffle 220 defines a large internal aperture (not shown) to permit the filling needle at the rearward end of the blunting member and the blunting member shuttle 24 to pass therethrough. A spring 54 is partially compressed between shuttle flanges 32 and baffle 220.

Figure 9C:
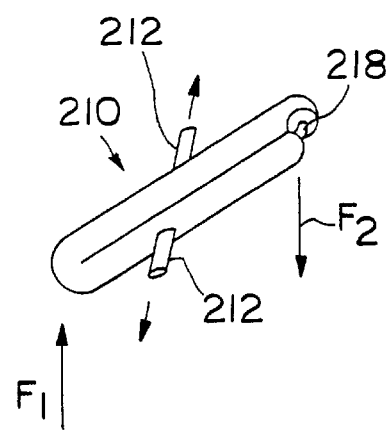
FIG. 9C is a perspective view of the ring lever 210 of FIG. 9B.

Actuator frame 230 is slidably disposed within shell 238. It will be apparent that the insertion of a sample collection tube that is pressed against transmitter baffle 220 will apply a force on bearing portion 218b of ring lever 210 at an end thereof opposite from pintle 218a, corresponding to force F1 (FIG. 9C). Ring lever 210 will rotate about studs 212 causing pintle 218a to move in the contrary direction indicated by arrow F2 (FIG. 9C). Since pintle 218a engages the slidable actuator frame 230, the upward (as sensed in FIG. 9A) movement of baffle 220 produces a contrary, downward motion of frame 230.

Actuator frame 230 is configured similarly to actuator ferrule 50 of mechanism 42 (FIG. 3) insofar as it permits the initial installation of needle assembly 30 in shell 238 in the sharp configuration while the mechanism remains in the pre-filling configuration of FIG. 9A. However, the internal configuration of actuator frame 230 will cause it to release detent 28 when it moves rearward (downward as sensed in FIG. 9A) in response to the first insertion of a sample tube into shell 238. Then, the needle is sharp while the device is in the filling configuration. Upon the subsequent removal of the sample collection tube, spring 54 will push shuttle 24 (and the actuator frame 230 bearing thereon) upward, thus moving the mechanism to the deployed configuration and the needle assembly (not fully shown) to the blunted configuration. The subsequent insertion of another sample tube will move baffle 220 upward and the resulting action of ring lever 210 will pull actuator frame 230 and shuttle 24 resting thereon downward in a direction contrary to the direction of insertion of the sample collection tube, moving the mechanism to the retracted configuration and the needle assembly to the sharpened configuration.

Figure 9D:
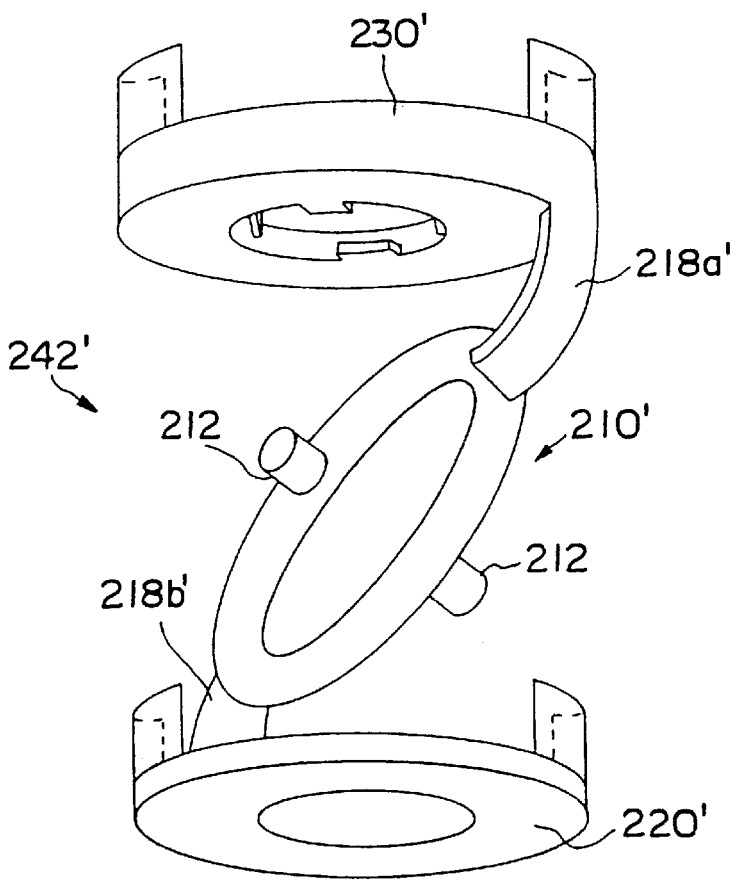
FIG. 9D is a perspective view of an alternative embodiment of a lever-type mechanism similar to the one of FIGS. 9A–9C.

In a related lever-type embodiment shown in FIG. 9D, mechanism 242' comprises a transmitter baffle 220', a ring lever 210' and an actuator 230' that are integrally interconnected by hinge straps 218a' and 218b' that are secured thereto. As shown in FIG. 9D, mechanism 242 may be considered a single piece. Hinge straps 218a', 218b' are sufficiently pliable to allow the necessary movement between lever 210' and draw transmitter baffle 220' and actuator 230' as lever 210' pivots to draw baffle 220' and actuator 230' towards each other and then push them apart. Strap hinges 218a' and 218b' may be formed, for example, from a polymeric material. Optionally, transmitter baffle 220' and/or actuator 230' may be formed from the same material as the hinge strap connected thereto and they may be molded together with the hinge strap in a single operation, leaving a distal end of the strap hinge free to be secured to another structure of mechanism 242'. For example, lever 210' may be formed with hinge straps 218a' and 218b' extending therefrom, and the distal ends of the straps may be secured to baffle 220' and actuator 230' by any suitable method, e.g., by adhesive, sonic welding, etc. Alternatively, mechanism 242' might be formed as a whole in a single molding operation.

Figure 10A:
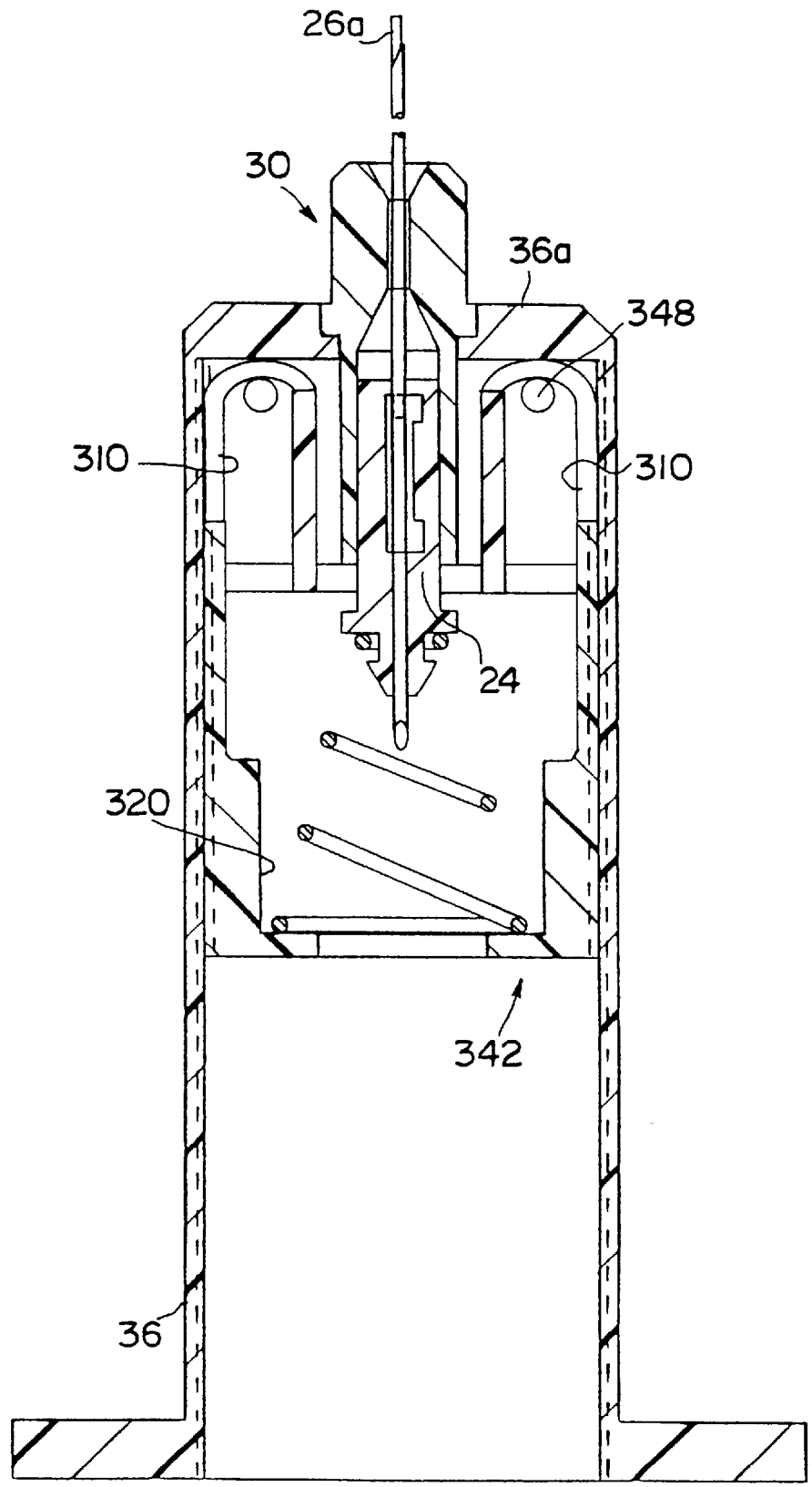
FIGS. 10A and 10B are schematic cross-sectional views of a blood collection needle in accordance with still another embodiment of the present invention.
Figure 10B:
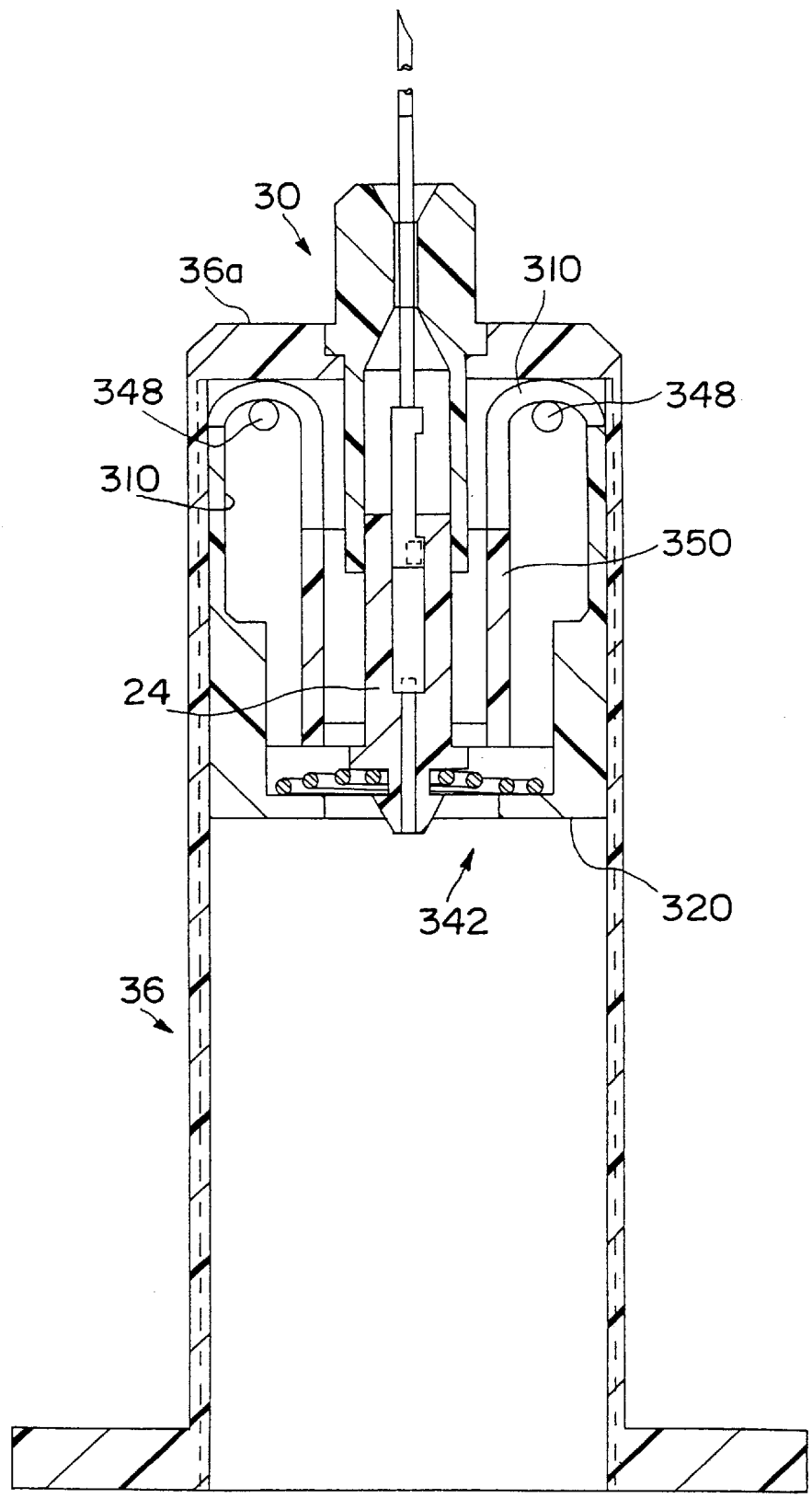

According to yet another embodiment of the invention, a mechanism 342 shown in FIG. 10A comprises pliable, resilient straps 310 connecting a transmitting ferrule 320 and an actuator ferrule 350. Straps 310 are configured to have a reverse bend about pins 348, and so extend forward from the forward edge of transmitting sleeve 320, around pins 348 to actuator ferrule 350, from which it extends forward as well. In the region of the reverse bend around pins 348, straps 310 may slidably bear against the interior of forward end 36a of holder 36. FIG. 10A shows the device in a blunted configuration corresponding to the configuration shown in FIG. 4B. When a collection tube is inserted into holder 36, transmitting sleeve 320 is moved forward in holder 36, pushing straps 310 against the forward end 36a of holder 36. Straps 310 loop around pins 348 and push actuator ferrule 350 rearward, unlocking needle assembly 30 and pulling shuttle 24 to a retracted position as shown in FIG. 10B, placing the device in a sharpened configuration. Thus, straps 310 constitute a reversing link between the transmitting sleeve 320 and the actuator ferrule 350, performing an equivalent function to the gear and toothed splines of the embodiment of FIG. 3.

While the invention has been described in detail with reference to particular embodiments thereof, it will be apparent that upon a reading and understanding of the foregoing, numerous alterations to the described embodiments will occur to those skilled in the art and it is intended to include such alterations within the scope of the appended claims.

What is claimed is:

1. A needle holder apparatus comprising:
a holder for a needle assembly having a needle cannula and a movable blunting member, the holder being dimensioned and configured for receiving and holding a sample collection tube in fluid flow communication with such needle assembly; and
a mechanism in the holder comprising a movable actuator member configured and situated for engaging a blunting member, a movable transmitter member, and means for moving the actuator in the holder in opposite directions from that of the transmitter member.

2. The apparatus of claim 1 further comprising a biasing member positioned to be tensioned against the transmitter member when the transmitter member and the actuator member move in the holder, to bias the mechanism to reverse such motion.

3. The apparatus of claim 1 or claim 2 wherein the holder comprises a shell having a cylindrical interior and wherein the reversing link member comprises a cylindrical cam member rotatably disposed in the holder, the reversing link member comprising a pair of counter-spiraled cam regions, wherein the transmitter member engages one cam region and the actuator member engages the other cam region.

4. The apparatus of claim 1 or claim 2 wherein the reversing link member comprises a pinion and wherein the transmitter member and the actuator member each comprise a rack for engaging the pinion.

5. The apparatus of claim 1 or claim 2 wherein the reversing link member comprises a lever pivotably mounted in the holder for rotation about a fulcrum point, the lever having two arms extending from the fulcrum point, one arm being attached to the transmitter member and the other arm being connected to the actuator member.

6. The apparatus of claim 1 or claim 2 wherein the reversing link member comprises a pliable, resilient strap.

7. A blood collection needle comprising:
a needle assembly comprising a needle cannula and a blunting member, the needle cannula having a puncture tip and having a needle passageway therethrough and the blunting member having a blunt end, the needle cannula and the blunting member being disposed telescopically one within the other without obstructing flow through the needle passageway, the needle assembly being movable between an insertion configuration in which the puncture tip of the needle cannula is exposed and a blunted configuration in which the blunt end of the blunting member extends beyond the puncture tip to blunt the apparatus;
a holder in which the needle assembly is mounted with the needle cannula in fixed relation to the holder, the holder being dimensioned and configured for receiving and holding a sample collection tube in fluid flow communication with the needle assembly; and
means for moving the needle assembly into the insertion configuration when a collection tube is installed in the holder and into the blunted configuration when the collection tube is removed from the holder.

8. A blood collection needle comprising:
a needle assembly comprising a needle cannula and a blunting member, the needle cannula having a puncture tip and having a needle passageway therethrough and the blunting member having a blunt end, the needle cannula and the blunting member being disposed telescopically one within the other without obstructing flow through the needle passageway, and being movable between a sharpened configuration in which the puncture tip of the needle cannula is exposed and a blunted configuration in which the blunt end of the blunting member extends beyond the puncture tip to blunt the apparatus;
a holder in which the needle assembly is mounted with the needle cannula in fixed relation to the holder, the holder being dimensioned and configured for receiving and holding a sample collection tube in fluid flow communication with the needle assembly; and
a mechanism comprising an actuator member configured and situated for engaging the blunting member, a transmitter member situated to engage a sample collection tube as it is installed in the holder, and a reversing link member that engages the actuator member and the transmitter member and that causes the actuator to move in an opposite direction from that of the transmitter member.

9. The blood collection needle of claim 8 further comprising a biasing member positioned to be tensioned against the transmitter member when a collection tube is installed in the holder to bias the mechanism to the blunted configuration.

10. The blood collection needle of claim 8 wherein the holder comprises a shell having a cylindrical interior and wherein the reversing link member comprises a cylindrical cam member rotatably disposed in the holder, the reversing link member comprising a pair of counter-spiraled cam regions, wherein the transmitter member engages one cam region and the actuator member engages the other cam region.

11. The blood collection needle of claim 8 wherein the reversing link member comprises a pinion and wherein the transmitter member and the actuator member each comprise a rack for engaging the pinion.

12. The blood collection needle of claim 8 wherein the reversing link member comprises a lever pivotably attached to the transmitter member and to the actuator member, the lever being mounted in the holder for rotation about a fulcrum axis that is between the points of attachment of the transmitter member and the actuator member.

13. The blood collection needle of claim 8 wherein the reversing link member comprises a pliable, resilient strap.

14. The blood collection needle of any one of claims 8–13 further comprising locking means for locking the needle assembly in the blunted configuration.

15. The blood collection needle of any one of claims 8–13 further comprising a resilient detent mounted on one of the needle and the blunting member and a notch in the other, wherein the needle assembly is configured so that the detent engages the groove when the device is in the blunted configuration.

16. The blood collection needle of claim 15 wherein one of the actuator member, the transmitter member and the reversing link member is configured to disengage the detent from the notch in response to the movement of the actuator member towards the insertion configuration.

17. A blood collection needle comprising:
a needle assembly comprising a needle cannula and a blunting member, the needle cannula having a puncture tip and having a needle passageway therethrough and the blunting member having a blunt end, the needle cannula and the blunting member being disposed telescopically one within the other without obstructing flow through the needle passageway, and being movable between a sharpened configuration in which the puncture tip of the needle cannula is exposed and a blunted configuration in which the blunt end of the blunting member extends beyond the puncture tip to blunt the apparatus;
a holder in which the needle assembly is mounted with the needle cannula in fixed relation to the holder, the holder being dimensioned and configured for receiving and holding a sample collection tube in fluid flow communication with the needle assembly, the holder having a cylindrical interior;
an actuator that is movably disposed in the holder and that engages the blunting member whereby movement of the actuator can move the blunting member between the blunted configuration and the sharpened configuration;
a link member having a cylindrical exterior and defining a pair of counter-spiraled cam regions comprising first and second link cam regions, the link member being situated in the holder for rotation therein and for engagement of the first link cam region by the actuator;
a transmitter that engages the second link cam region and that is positioned to engage a sample collection tube installed in the holder; and
a resilient biasing member that engages the actuator and the transmitter and that biases the actuator to move the blunting member to the blunted configuration;
the actuator, link member and transmitter being configured so that the blunting member is in the sharpened configuration when a tube is installed in the holder and is moved to the blunted configuration when the tube is withdrawn from the holder.

18. A blood collection needle comprising:

a needle assembly comprising a needle cannula and a blunting member, the needle cannula having a puncture tip and having a needle passageway therethrough and the blunting member having a blunt end, the needle cannula and the blunting member being disposed telescopically one within the other without obstructing flow through the needle passageway, and being movable between a sharpened configuration in which the puncture tip of the needle cannula is exposed and a blunted configuration in which the blunt end of the blunting member extends beyond the puncture tip to blunt the apparatus;

a holder in which the needle assembly is mounted with the needle cannula in fixed relation to the holder, the holder being dimensioned and configured for receiving and holding a sample collection tube in fluid flow communication with the needle assembly, the holder having a cylindrical interior;

an actuator that is movably disposed in the holder and that is configured and situated for engaging the blunting member whereby movement of the actuator can move the blunting member between the blunted configuration and the sharpened configuration, the actuator comprising a rack;

a transmitter positioned in the holder for engaging a sample collection tube installed in the holder, the transmitter comprising a rack; and a pinion rotatably mounted in the holder in toothed engagement with the transmitter rack and with the actuator rack; and a resilient biasing member positioned to be tensioned against the transmitter when a sample collection tube is installed in the holder to bias the actuator to move the blunting member to the blunted configuration;

the actuator, pinion and transmitter being configured so that the blunting member is moved to the blunted configuration when the tube is withdrawn from the holder.

19. A blood collection needle comprising:

a needle assembly comprising a needle cannula and a blunting member, the needle cannula having a puncture tip and having a needle passageway therethrough and the blunting member having a blunt end, the needle cannula and the blunting member being disposed telescopically one within the other without obstructing flow through the needle passageway, and being movable between a sharpened configuration in which the puncture tip of the needle cannula is exposed and a blunted configuration in which the blunt end of the blunting member extends beyond the puncture tip to blunt the apparatus;

a holder in which the needle assembly is mounted with the needle cannula in fixed relation to the holder, the holder having a cylindrical interior and being dimensioned and configured for receiving and holding a sample collection tube in fluid flow communication with the needle assembly;

an actuator that is movably disposed in the holder and that is configured and situated for engaging the blunting member whereby movement of the actuator can move the blunting member between the blunted configuration and the sharpened configuration;

a transmitter positioned in the holder for engaging a sample collection tube installed in the holder;

a lever pivotably mounted in the holder at a fulcrum point on the lever, the lever having arms extending from the fulcrum point, one arm being connected to the transmitter and another arm being connected to the actuator; and a resilient biasing member that engages the actuator and the transmitter and that biases the actuator to move the blunting member to the blunted configuration;

the actuator, lever and transmitter being configured so that the blunting member is moved to the blunted configuration when the tube is withdrawn from the holder.

20. A blood collection needle comprising:

a needle assembly comprising a needle cannula and a blunting member, the needle cannula having a puncture tip and having a needle passageway therethrough and the blunting member having a blunt end, the needle cannula and the blunting member being disposed telescopically one within the other without obstructing flow through the needle passageway, and being movable between a sharpened configuration in which the puncture tip of the needle cannula is exposed and a blunted configuration in which the blunt end of the blunting member extends beyond the puncture tip to blunt the apparatus;

a holder in which the needle assembly is mounted with the needle cannula in fixed relation to the holder, the holder being dimensioned and configured for receiving and holding a sample collection tube in fluid flow communication with the needle assembly;

an actuator that is configured and situated for engaging the blunting member whereby movement of the actuator can move the blunting member between the blunted configuration and the sharpened configuration;

a transmitter positioned in the holder for engaging a sample collection tube installed in the holder;

a reversing strap connected at one point to the actuator and at another point to the transmitter and having a bent configuration between the points of connection;

a resilient biasing member that engages the actuator and the transmitter and that biases the actuator to move the blunting member to the blunted configuration;

the actuator, reversing strap and transmitter being configured so that the blunting member is moved to the blunted configuration when the tube is withdrawn from the holder.

21. A method for taking at least one blood sample, comprising:

(a) inserting a needle cannula into a patient's tissue;

(b) disposing a first sample collection tube in fluid flow communication with the needle cannula to deliver a sample of blood into the tube; and (c) removing the first sample collection tube from the needle cannula after a sample is delivered thereto and blunting the needle as the first sample collection tube is being removed.

22. The method of claim 21 wherein the step (b) comprises inserting the sample collection tube in a holder for the needle cannula and engaging and moving a transmitter in the holder with the sample collection tube, and wherein step (c) comprises withdrawing the sample collection tube from the holder.

23. The method of claim 21 further comprising (d) disposing at least one subsequent sample collection tube in fluid flow communication with the needle cannula and sharpening the needle cannula and then, after a sample is delivered into the subsequent sample collection tube, and (e) withdrawing the subsequent sample collection tube and blunting the needle cannula.

* * * * *